US005455239A

United States Patent [19]

Cama et al.

[11] Patent Number: 5,455,239

[45] Date of Patent: Oct. 3, 1995

[54] 3-ARYL OF HETEROARYL-7-HETEROARALKYLAMIDO CEPHALOSPORIN COMPOUNDS, COMPOSITIONS AND METHODS OF USE

[75] Inventors: Lovji D. Cama, Tenafly; James V. Heck, Scotch Plains, both of N.J.

[73] Assignee: Merck & Co. Inc., Rahway, N.J.

[21] Appl. No.: 102,439

[22] Filed: Aug. 5, 1993

[51] Int. Cl.$^{6}$ .................... C07D 501/22; A61K 31/545

[52] U.S. Cl. .................... 514/202; 514/206; 540/222; 540/225

[58] Field of Search .................... 540/222, 225, 540/227; 514/202, 206; 501/202, 206

[56] References Cited

U.S. PATENT DOCUMENTS

| | | | |
|---|---|---|---|
| 3,843,641 | 10/1974 | Christensen et al. | 260/243 C |
| 3,925,363 | 12/1975 | Cama | 260/239.1 |
| 4,014,873 | 3/1977 | Christensen et al. | 260/243 C |
| 4,035,359 | 7/1977 | Christensen et al. | 260/239.1 |
| 4,041,029 | 8/1977 | Firestone et al. | 544/29 |
| 4,058,661 | 11/1977 | Cama et al. | 544/21 |
| 4,071,529 | 1/1978 | Christensen et al. | 260/306.7 C |
| 4,102,882 | 7/1978 | Firestone et al. | 260/239.1 |
| 4,107,432 | 8/1978 | Christensen et al. | 544/21 |
| 4,123,528 | 10/1978 | Cama et al. | 424/248.52 |
| 4,150,156 | 4/1979 | Beattie et al. | 424/246 |
| 4,154,845 | 5/1979 | Christensen et al. | 424/271 |
| 4,218,459 | 8/1980 | Cama et al. | 424/270 |
| 4,219,462 | 8/1980 | Christensen et al. | 260/245.2 P |
| 4,267,188 | 5/1981 | Cama et al. | 424/274 |
| 4,321,197 | 3/1982 | Cama et al. | 260/245.2 T |
| 4,324,890 | 4/1982 | Christensen et al. | 544/21 |
| 4,338,437 | 7/1982 | Christensen et al. | 544/21 |
| 4,595,750 | 6/1986 | Christensen et al. | 544/90 |
| 4,617,152 | 10/1986 | Christensen et al. | 540/200 |
| 4,734,497 | 3/1988 | Christensen et al. | 540/200 |
| 4,755,669 | 10/1988 | Cama et al. | 514/210 |
| 5,276,024 | 1/1994 | Schneider et al. | 514/202 |

FOREIGN PATENT DOCUMENTS

560365A1 9/1993 European Pat. Off. .

*Primary Examiner*—Nicholas Rizzo
*Attorney, Agent, or Firm*—Richard C. Billups; Mark R. Daniel; Joseph F. DiPrima

[57] ABSTRACT

A compound of the formula I is disclosed.

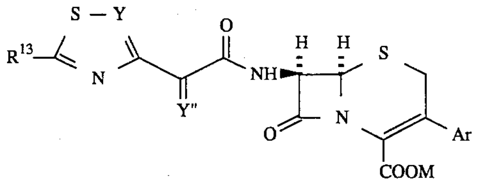

$R^{13}$ represents hydrogen, $NH_2$, C1–4 alkyl, C1–4 alkylamino or di(C1–4) alkylamino-;

Y represents CH or N;

Y" represents (a) $CR^{y'}R^{z'}$ with $R^{y'}$ and $R^{z'}$ hydrogen, C1–6 alkyl, $C_{3-8}$ cycloalkyl or $C_{1-6}$ alkyl substituted with $C_{3-8}$ cycloalkyl, or (b) N substituted with $OR^{14}$ with $R^{14}$ representing H, $C_{1-4}$ alkyl or $C_{1-4}$ alkyl substituted with COOH. Ar represents:

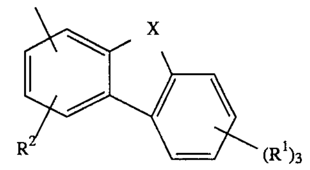

One of $R^1$ and $R^2$ independently represent H, W as defined below or one of the groups (a) through (d) below, and the other represents H or W. Pharmaceutical compositions and methods of use are also included.

19 Claims, No Drawings

3-ARYL OF HETEROARYL-7-HETEROARALKYLAMIDO CEPHALOSPORIN COMPOUNDS, COMPOSITIONS AND METHODS OF USE

BACKGROUND OF THE INVENTION

The present invention relates to antibacterial agents of the cephalosporin class in which the six membered ting of the cephalosporin nucleus is substituted with an aryl or heteroaryl group at position three.

Cephoxitin was an early cephalosporin antibacterial agent having a broad spectrum; it has the following formula:

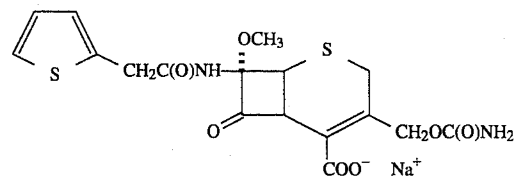

The cephalosporins of the present invention have activity against gram positive and gram negative microorganisms, and are believed to be useful against methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy for these difficult to control pathogens.

Moreover, there is an increasing need for agents effective against such pathogens (MRSA/MRCNS) which are at the same time relatively free from undesirable side effects. And, the current agent of choice, vancomycin, a glycopeptide antibacterial, is experiencing an ever increasing amount of resistance in the MRSA/MRCNS pathogens.

SUMMARY OF THE INVENTION

The present invention addresses a compound represented by formula I:

I

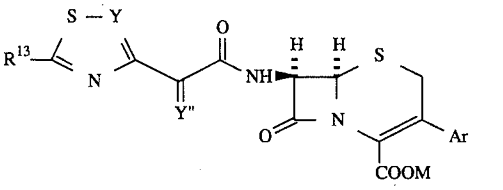

or a pharmaceutically acceptable salt or solvate thereof.

$R^{13}$ represents hydrogen, $NH_2$, C1–4 alkyl, C1–4 alkylamino or a di (C1–4) alkylamino- group.

Y represents CH or N.

Y" represents (a) $CR^{y'}R^{z'}$ wherein $R^{y'}$ and $R^{z'}$ independently represent H, C1–6 alkyl, C3–8 cycloalkyl or C1–6 alkyl substituted with C3–8 cycloalkyl, or (b) N substituted with $OR^{14}$ with $R^{14}$ equal to H, C1–C4 alkyl or C1-C4 alkyl substituted with COOH.

Ar represents:

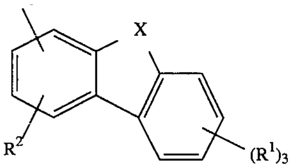

in which X is either present or absent. When present, X represents $—CH_2—$, $—CH_2CH_2—$, $—C{=}N—$, —C(O)—, —O— or $—S(O)_x—$ with x equal to 0, 1 or 2.

One of $R^1$ and $R^2$ represents hydrogen, W as defined below or one of the groups (a) through (d) below, and the other represents hydrogen or W:

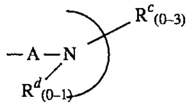
(a)

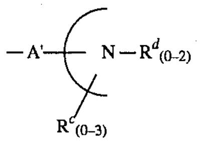
(b)

$—Ap—NR^{10}R^{11}R^{12}{}_{(0\text{-}1)}$; (c)

and

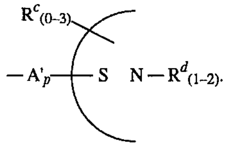
(d)

Each R' group is defined independently.

When one of $R^1$ and $R^2$ represents (a)

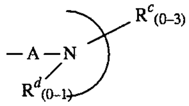

A represents $—(CR^{3'}R^{4'})_r—Q—(CR^{3'}R^{4'})_s—$ wherein r represents an integer of from 0–6, and s represents an integer of from 1–6. Q represents a covalent bond, —O—, $—S(O)_x—$ with x equal to 0, 1 or 2,$—NR^{3'}—$, $—SO_2NR^{3'}—$, $—NR^{3'}SO_2—$, $—C(O)NR^{3'}—$, —NRYC(O)—, $—CR^{3'}{=}CR^{4'}—$, —C(O)— or —OC(O)—.

$R^{3'}$ and $R^{4'}$ independently represent H or C1–4 lower alkyl, and $(CR^{3'}R^{4'})_s—$ is attached to the ring nitrogen.

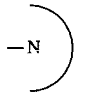

represents a 5 or 6 membered monocyclic heterocycle or an 8–10 membered bicyclic heterocycle, bonded to A through the ring nitrogen and having a substituent group $R^d$ optionally attached to the ting nitrogen, and having 0–3 $R^c$ groups attached to other atoms of the heterocyclic group. The ting nitrogen is tertiary or quaternary by virtue of the ring bonds and $R^d$ group which may be attached. The heterocyclic group is saturated or unsaturated, and may be aromatic, partially aromatic or non-aromatic.

The heterocycle may also contain 0–3 additional nitrogen atoms and 0–1 oxygen or sulfur atom.

Each $R^c$ independently represents H, W as defined below or $NR^yR^z$. $R^y$ and $R^z$ independently represent H, C1 to C4 alkyl, C1 to C4 alkyl substituted with $R^q$, or $R^y$ and $R^z$ are taken together to represent either a 3- to 5- membered alkylidene radical to form a ring, optionally substituted with $R^q$, or a 2- to 4- membered alkylidene radical interrupted by O or $S(O)_x$ with x equal to 0, 1 or 2, to form a ring, said alkylidene being optionally substituted with $R^q$ as defined below.

Each $R^d$ independently represents hydrogen, $NH_2$, O— or C1 to C4 alkyl, optionally mono-substituted with $R^q$ as defined below.

$R^q$ is selected from the group consisting of hydroxy, methoxy, cyano, —C(O)$NH_2$, —OC(O)$NH_2$, —CHO, —OC(O)$N(CH_3)_2$, —$SO_2NH_2$, —$SO_2N(CH_3)_2$, —S(O)$CH_3$, —$SO_2CH_3$, —F, —$CF_3$, —$SO_3M^b$ with $M^b$ representing H or alkali metal; tetrazolyl (where the point of attachment is the carbon atom of the tetrazole ring and one of the nitrogen atoms is optionally mono-substituted by another $R^q$ group as defined above) and —$CO_2M^a$, where $M^a$ is H, alkali metal, methyl or phenyl.

When one $R^1$ and $R^2$ represents (b)

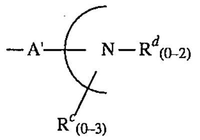

A' represents —$(CR^{3'}R^{4'})_{m'}$—Q—$(CR^{3'}R^{4'})_{m'}$—with each m' independently equal to 0–6, and Q, $R^{3'}$ and $R^{4'}$ are as defined above, except that when each m' is 0, Q is not a covalent bond, and —$(CR^{3'}R^{4'})_{m'}$ is attached to the phenyl ring.

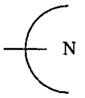

represents a 5 or 6 membered monocyclic heterocycle or a saturated 8–10 membered bicyclic heterocycle, said heterocycle being unsaturated and aromatic, partially aromatic or non-aromatic, bonded to A' through an atom other than the ring nitrogen and having 0–2 $R^d$ substituent groups attached to the ting nitrogen. The nitrogen in the heterocycle is tertiary or quaternary by virtue of the ring bonds and the $R^d$ groups which may be attached.

The heterocycle further contains 0–1 oxygen or sulfur atom and 0–2 additional nitrogen atoms therein.

$R^c$ and $R^d$ are as defined above.

When one of $R^1$ and $R^2$ represents (c) —$A_p$—$NR^{10}R^{11}R^{12}{}_{(0-1)}$;

A is as defined above and p is an integer 0 or 1.

$R^{10}$, $R^{11}$ and where present, $R^{12}$, independently represent hydrogen, C1–4 alkyl or $C^{1-4}$ alkyl optionally mono-substituted with $R^q$.

Alternatively, $R^{10}$, $R^{11}$ and $R^{12}$ may be taken in combination to represent a C4 to C10 alkanetriyl group, optionally substituted with up to three. W groups, with W as defined below;

The nitrogen atom to which said $R^{10}$, $R^{11}$ and $R^{12}$ groups are attached is tertiary or quaternary.

When one of $R^1$ and $R^2$ represents (d)

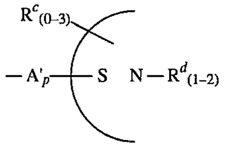

A', p, $R^c$ and $R^d$ are as previously defined.

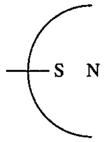

represents a saturated 5 or 6 membered monocyclic heterocycle or a saturated 8–10 membered bicyclic heterocycle, bonded to A through an atom other than the ring nitrogen. One or two $R^d$ substituent groups are attached to the ring nitrogen. The nitrogen in the heterocycle is tertiary or quaternary by virtue of the ting bonds and the $R^d$ groups which are attached.

W represents a member selected from the group consisting of:

a) trifluoromethyl group: —$CF_3$;

b) a halogen atom: —Br, —Cl, —F, or —I;

c) C1–C4 alkoxy radical: —OC1–4 alkyl, wherein the alkyl is optionally mono-substituted by $R^q$, where $R^q$ is as defined above;

d) a hydroxy group: —OH;

e) a carbonyloxy radical: —OC(O)$R^s$, where $R^s$ is C1–4 alkyl or phenyl, each of which is optionally mono-substituted by $R^q$ as defined above;

f) a carbamoyloxy radical; —OC(O)N($R^y$)$R^z$, where $R^y$ and $R^z$ are independently H, C1–4 alkyl, (optionally mono-substituted by $R^q$ as defined above), or are taken together to represent a 3- to 8-membered alkylidene radical which forms a ting (optionally substituted with $R^q$ as defined above), or a 2- to 4-membered alkylidene radical interrupted by —O—, —S—, —S(O)— or —$S(O)_2$— which forms a ring, said ring being optionally mono-substituted with $R^q$ as defined above;

g) a sulfur radical: —$S(O)_n$—$R^s$, where n=0–2, and $R^s$ is defined above;

h) a sulfamoyl group: —$SO_2N(R^y)R^z$, where $R^y$ and $R^z$ are as defined above;

i) azido: $N_3$ j) a formamido group: —N($R^t$)C(O)H, where $R^t$ is H or C1–4 alkyl, said alkyl group being optionally mono-substituted with $R^q$ as defined above;

k) an alkylcarbonylamino radical: —N($R^t$)C(O)C1–4 alkyl, wherein $R^t$ is as defined above;

l) an alkoxycarbonylamino radical:

. —N($R^t$)C(O)OC1–4 alkyl, where $R^t$ is as defined above;

m) a ureido group: —N($R^t$)C(O)N($R^y$)$R^z$ where $R^t$, $R^y$ and $R^z$ are defined above;

n) a sulfonamido group: —N($R^t$)$SO_2R^s$, where $R^s$ and $R^t$ are as defined above;

o) a cyano group: —CN;

p) a formyl or acetalized formyl radical: —C(O)H or —$CH(OCH_3)_2$;

q) an alkylcarbonyl radical wherein the carbonyl is acetalized: —$C(OCH_3)_2$ C1–C4 alkyl, where the alkyl is optionally mono-substituted by $R^q$ as defined above;

r) a carbonyl radical: —C(O)$R^s$, where $R^s$ is as defined above;

s) a hydroximinomethyl radical in which the oxygen or carbon atom is optionally substituted by a C1–C4 alkyl group: —(C=NO$R^z$)$R^y$ where $R^y$ and $R^z$ are as defined above, except they may not be joined together to form a ring;

t) an alkoxycarbonyl radical: —C(O)OC1–4 alkyl, where the alkyl is optionally mono-substituted by $R^q$ as defined above;

u) a carbamoyl radical: —C(O)N($R^y$)$R^z$, where $R^y$ and $R^z$ are as defined above;

v) an N-hydroxycarbamoyl or N(C1–C4 alkoxy)carbamoyl radical in which the nitrogen atom may be additionally substituted by a C1–C4 alkyl group: —C(O)N(O$R^y$)$R^z$, where $R^y$ and $R^z$ are as defined above, except they may not be joined together to form a ring;

w) a thiocarbamoyl group: —C(S)N($R^y$)$R^z$ where $R^y$ and $R^z$ are as defined above;

x) carboxyl: —COO$M^a$ where $M^a$ is as defined above;

y) thiocyanate: —SCN;

z) trifluoromethylthio: —$SCF_3$;

aa) tetrazolyl, where the point of attachment is the carbon atom of the tetrazole ring and one of the nitrogen atoms is mono-substituted by hydrogen, an alkali metal or a C1–C4 alkyl optionally substituted by $R^q$ as defined above;

ab) an anionic function selected from the group consisting of:

phosphono [P=O($OM^a$)$_2$]; alkylphosphono {P=O($OM^a$)—[O(C1–C4 alkyl)]}; alkylphosphinyl [P=O($OM^a$)—(C1–C4 alkyl)]; phosphoramido [P=O($OM^a$)N($R^y$)$R^z$ and P=O($OM^a$)NH$R^x$]; sulfino ($SO_2M^a$); sulfo ($SO_3M^a$); acylsulfonamides selected from the structures $SO_2NM^a$CON($R^y$)$R^z$; and $SO_2NM^a$CN, where $R^x$ is phenyl or heteroaryl, where heteroaryl is a monocyclic, aromatic hydrocarbon group having 5 or 6 ring atoms, in which a carbon atom is the point of attachment, one of the carbon atoms has been replaced by a nitrogen atom, one additional carbon atom is optionally replaced by a heteroatom selected from O or S, and from 1 to 2 additional carbon atoms are optionally replaced by nitrogen heteroatoms, and where the phenyl and heteroaryl are optionally mono-substituted by $R^q$, said $R^q$, $M^a$, $R^y$ and $R^z$ are as defined above;

ac) a C5–C7 cycloalkyl group in which one of the carbon atoms in the ring is replaced by a heteroatom selected from O, S, NH, or N(C1–C4 alkyl) and in which one additional carbon may be replaced by the NH or N(C1–C4 alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) a C2–C4 alkenyl radical, optionally mono-substituted by one of the substituents a) to ac) above and phenyl which is optionally substituted by $R^q$ as defined above;

ae) a C2–C4 alkynyl radical, optionally mono-substituted by one of the substituents a) to ac) above;

af) a C1–C6 alkyl radical;

ag) a C1–C4 alkyl group mono-substituted by one of the substituents a)–ac) above;

ah) a C1–C6 alkyl group substituted with up to 3 groups selected from oxime (=N—O$R^{14}$), cycloalkyl, aryl, heterocycloalkyl, heteroaryl and C1–3 alkoxy groups with these groups as defined above;

ai) a 2-oxazolidinonyl moiety in which the point of attachment is the nitrogen atom of the oxazolidinone ring, the ring oxygen atom is optionally replaced by a heteroatom selected from S and N$R^t$ (where $R^t$ is as defined above) and one of the saturated carbon atoms of the oxazolidinone ring is optionally mono-substituted by one of the substituents a) to ag) above.

M represents hydrogen, a negative charge, a biolabile ester forming group, a carboxyl protecting group or a pharmaceutically acceptable cation.

Also included are pharmaceutical compositions which are comprised of a compound of formula I in combination with a pharmaceutically acceptable carrier.

Also included are methods of use which are comprised of administering to a mammal in need of such treatment a compound in accordance with formula I in an amount effective to treat a bacterial infection.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to t0 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, a) through ac) as defined above, at any available point of attachment. When the alkyl group is said to be substituted with an alkyl group, this is used interchangeably with "branched alkyl group".

Cycloalkyl is a form of alkyl containing from 3 to 15 carbon atoms, without double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight, branched or cyclic, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. Aryl thus contain at least one ring having at least 6 atoms, with up to five such rings being present, containing up to 22 atoms therein, with alternating (resonating) double bonds between adjacent carbon atoms. The preferred aryl groups are phenyl, naphthyl, fluorenonyl and phenanthrenyl. Aryl groups may likewise be substituted with $R^1$/$R^2$ groups as defined below. Preferred substituted aryls include phenyl and naphthyl substituted with one or two preferred $R^1$/$R^2$ groups.

The term "heteroaryl" refers to a monocyclic aromatic hydrocarbon group having 5 or 6 ring atoms, a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms, or a 3–5 ring system containing at least one heteroatom in one of the rings. Heteroaryl groups being optionally substituted with up to four $R^q$ groups.

Heteroaryl thus includes aromatic and partially aromatic groups which contain one or more heteroatoms. Examples of this type are pyrrole, pyridine, oxazole, thiazole and oxazine. Additional nitrogen atoms may be present together with the first nitrogen and oxygen or sulfur, giving, e.g., thiadiazole. The preferred heteroaryls are those where only nitrogen heteroatoms are present when there is more than one. Typical of these are pyrazole, tetrazole, imidazole, pyridine, pyrimidine and pyrazine and triazine.

The heteroaryl group of $R^x$ may be optionally substituted by $R^q$, as defined above, and substitution can be on one of the carbon atoms or one of the heteroatoms, although in the latter case certain substituent choices may not be appropriate.

The most preferred heteroaryl groups are the following:

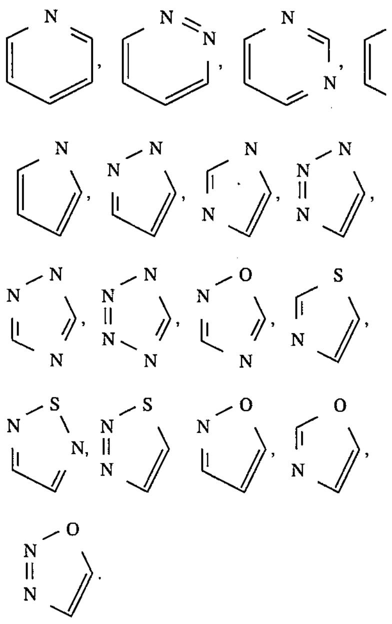

Additionally, any of the above rings can be fused to another ring, e.g., a phenyl ring.

The term "heterocycloalkyl" refers to a cycloalkyl group (nonaromatic) in which one of the carbon atoms in the ring is replaced by a heteroatom selected from O, S, NH, or N(C1–C4 alkyl), and in which up to three additional carbon atoms may be replaced by said hetero groups. The most preferred heterocycloalkyl groups are set forth below:

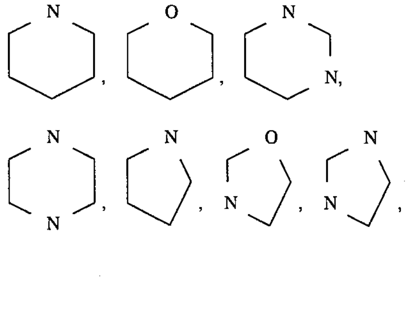

-continued

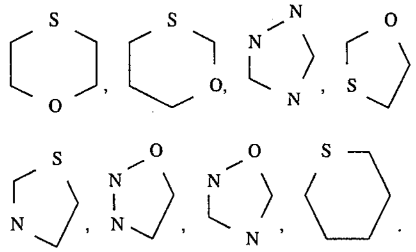

The term "quaternary nitrogen" refers to a tetravalent positively charged nitrogen atom including, e.g., the positively charged nitrogen in a tetraalkylammonium group (eg. tetramethylammonium, N-methylpyridinium), the positively charged nitrogen in a protonated ammonium species (eg. trimethylhydroammonium, N-hydropyridinium), the positively charged nitrogen in an amine N-oxide (eg. N-methylmorpholine-N-oxide, pyridine-N-oxide)., and the positively charged nitrogen in an N-amino-ammonium group (eg. N-aminopyridinium).

The term "heteroatom" means N, S, or O, selected on an independent basis.

Alkylene (alkylidene or alkanediyl) and arylene refer to the groups noted above with divalent points of attachment. For example, phenylene is an arylene group, attached at any of the 1, 2-1, 3- or 1, 4- positions. Examples of alkylene include $-CH_2-$, $-CH_2CH_2-$, $-CH_2CH_2CH_2-$, $-CH_2CHCH_3$ and $-CHCH_2CH_3$.

Similarly, alkanetriyl refers to an alkane-derived group with three points of attachment. Alkanetriyl groups contain from five to fifteen carbon atoms, which may be straight, branched, cyclic or multicyclic.

Aralkyl is a specie of substituted alkyl, containing up to three aryl groups substituted on a straight, branched or cycloalkyl group. The most preferred aralkyl group is benzyl.

Halogen, or "halo" refers to bromine, chlorine, fluorine and iodine.

Alkoxy refers to $C_1$–$C_4$ alkyl —O—, with the alkyl group optionally substituted with the variable $R^q$.

Carbonyloxy refers to the radical: $-OC(O)R^s$, where $R^s$ is $C_{1-4}$ alkyl or phenyl, each of which is optionally mono substituted by $R^q$.

Carbamoyloxy refers to the radical: $-OC(O)N(R^y)R^z$, where $R^y$ and $R^z$ are independently H, $C_{1-4}$ alkyl, (optionally mono-substituted by $R^q$ as defined above). Alternatively, $R^y$ and $R^z$ can be taken together to represent a 3- to 5-membered alkylidene radical which forms a ring (optionally substituted with $R^q$ as defined above), or a 2- to 4-membered alkylidene radical interrupted by —O—, —S—, —S(O)— or $-SO_2-$ which forms a ting, said ting being optionally mono-substituted with $R^q$ as defined above.

The term "sulfur radical" refers to the group: $-S(O)_x-R^s$, where x is an integer of from O to 2, and $R^s$ is as defined above.

The term "sulfamoyl group" refers to: $-SO_2N(R^y)R^z$, where $R^y$ and $R^z$ are as defined above, representing H, alkyl or alkyl mono-substituted with $R^q$.

The term "azido" refers to the group: $N_3$.

The term "formamido" refers to the group: $-N(R^t)C(O)H$, where $R^t$ is H or $C_{1-4}$ alkyl, said alkyl group being optionally mono-substituted with $R^q$ as defined above.

The term "alkylcarbonylamino" refers to the group: $—N(R^t)C(O)C_{1-4}$ alkyl, wherein $R^t$ is as defined above.

The term "alkoxycarbonylamino" refers to the group: $—N(R^t)C(O)OC_{1-4}$ alkyl, where $R^t$ is as defined above. The term "ureido" refers to the group: $—N(R^t)C(O)N(R^y)R^z$ where $R^t$, $R^y$ and $R^z$ are defined above.

The term "sulfonamido" refers to the group: $—N(R^t)SO_2R^s$, where $R^s$ and $R^t$ are as defined above.

The terms "formyl" and "acetalized formyl radical" refer to the groups: —C(O)H or $—CH(OCH_3)_2$, respectively. Thus, an alkylcarbonyl radical wherein the carbonyl is acetalized is of the formula: $—C(OCH_3)_2C_1–C_4$ alkyl, where the alkyl is optionally mono-substituted by $R^q$.

A "carbonyl radical" is represented by the formula: $—C(O)R^s$, where $R^s$ is as defined above.

A "hydroximinomethyl" radical in which the oxygen or carbon atom is optionally substituted by a $C_1–C_4$ alkyl group is represented by the formula: $—(C{=}NOR^z)R^y$ where $R^y$ and $R^z$ are as defined above, except they may not be joined together to form a ring.

An "alkoxycarbonyl" radical is represented by the formula: $—C(O)OC_{1-4}$ alkyl, where the alkyl is optionally mono-substituted by $R^q$ as defined above.

A "carbamoyl" radical is represented by the formula: $—C(O)N(R^y)R^z$, where $R^y$ and $R^z$ are as defined.

An N-hydroxycarbamoyl or N($C_1–C_4$ alkoxy)carbamoyl radical in which the nitrogen atom may be additionally substituted by a $C_1–C_4$ alkyl group is represented by the formula: $—C(O)N(OR^y)R^z$, where $R^y$ and $R^z$ are as defined above, except they may not be joined together to form a ring.

A "thiocarbamoyl group" is represented by the structural formula: $—C(S)N(R^y)R^z$ where $R^y$ and $R^z$ are as defined above.

A "carboxyl group" is represented by the structural formula: $—COOM^a$ where $M^a$ is as defined above.

The term "tetrazolyl" is a heteroaryl group where the point of attachment is the carbon atom of the tetrazole ring and one of the nitrogen atoms is optionally mono-substituted by an alkali metal or a $C_1$–C4 alkyl optionally substituted by $R^q$.

The term "anionic function" refers to the members of the group: phosphono $[P{=}O(OM^a)_2]$; alkylphosphono $\{P{=}O(OM^a)—[O(C_1–C_4\ alkyl)]\}$; alkylphosphinyl $[P{=}O(OM^a)—(C_1–C4alkyl)]$; phosphoramido $[P{=}O(OM^a)N(R^y)R^z$ and $P{=}O(OM^a)NHR^x]$; sulfino $(SO_2M^a)$; sulfo $(SO_3M^a)$; acylsulfonamides selected from: $SO_2NM^aCON(R^y)R^z$; and $SO_2NM^aCN$, where $R^x$ is phenyl or heteroaryl.

Variables $R^3$ and $R^4$ independently represent H or lower alkyl.

One of the $R^1$ and $R^2$ groups represents H, W or an uncharged or a positively charged nitrogen containing group (a) through (d) as described above. The other R variable represents an uncharged specie selected from. H and W.

The values of (a) through (d) shown above are in charged or uncharged form. The particular nitrogen containing group is drawn as having three points of attachment, such as by attachment to the A moiety, ting bonds, and $R^d$ group or groups. In many instances, the nitrogen containing group is charged, such as when (c) is present and the nitrogen atom is substituted with $R^{10}$, $R^{11}$ and $R^{12}$. It is understood that when the moiety is positively charged, four points of attachment for the nitrogen exist, and the plus charge is present on the nitrogen atom.

When one of the R variables represents group (a), the spacer moiety —A— forms an alkylene chain, optionally containing a heteroatom or functional group, represented by —Q—. The length of A ranges from a methylene group to an alkyl chain of 12 carbon atoms in length, optionally also containing —Q— noted above. The —A— moiety bonds to the nitrogen containing ring through the N shown, and to the phenyl ring shown.

The heterocyclic group to which —A— bonds may be a heteroaryl group, a partially aromatic heterocycle or a non-aromatic heterocycle, with a substituent $R^d$ optionally bonded to the ting nitrogen. Hence, the heterocycle may be unsaturated or saturated. When the heterocycle is aromatic, the ring nitrogen is positively charged by virtue of the attachment to —A—, the ring bonds and Rd.

The heterocyclic group may also optionally contain up to three additional nitrogen atoms and up to one oxygen or sulfur atom. The heterocycle can also be substituted with up to three $R^c$ groups at any available points of attachment, either via carbon or nitrogen atoms.

When one of R 1 and $R^2$ represents group (b), the spacer moiety is optional; where present, —A'— represents an alkylene group, optionally interrupted with a heteroatom, Q. The ring structure is bonded to —A'— through an atom other than a ring nitrogen. The heterocycle is unsaturated and can be aromatic, partially aromatic or non-aromatic. The ring nitrogen is optionally substituted with one or two groups $R^d$, as desired. When the ting is aromatic and one $R^d$ is present on the ring nitrogen, the nitrogen is positively charged. When the ring is non-aromatic and there are two $R^d$ groups present, the nitrogen is positively charged. Hence, the nitrogen may have up to two $R^d$ groups present thereon, depending on the particular configuration desired.

Also, as described above with respect to the heterocycle in (a), up to three $R^c$ groups may be substituted onto the ring, at any available point of attachment.

When any of the variables and substituent groups are shown with bonds attached, e.g., —A—, $—R^c$, etc., this is to serve as a point of reference for application to the generic structure, and does not indicate that double or triple bonds are intended, unless such bonds are drawn.

When one of the R variables represents group (c), the spacer moiety —A— represents an optional alkylene group, which in turn is optionally interrupted with Q, which may be a heteroatom, substituted amine, sulfonamide and the like, as described above with respect to group (a). The nitrogen bound to the —A— spacer moiety is tertiary or quaternary by virtue of the $R^{10}$, $R^{11}$ and $R^{12}$ groups present thereon and —A— attached thereto. These R groups may independently represent H, alkyl or substituted alkyl groups.

Alternatively, $R^{10}$, $R^{11}$ and $R^{12}$ may be taken in combination to represent a $C_4$ to $C_{10}$ alkanetriyl group, bonded to the nitrogen. Thus, the nitrogen is quaternary.

When one of the $R^1$ and $R^2$ variables represents group (d), —A'— is as defined above for group (b). The spacer moiety is optional and when present, is attached to the heterocyclic moiety through an atom in the ring other than the nitrogen atom which is shown.

The nitrogen containing ting is saturated, and may be unsubstituted or substituted. The nitrogen may be quaternary with one or two $R^d$ groups as desired, or it may be tertiary.

One of the $R^1$ and $R^2$ variables represents H, W or a group selected from (a) through (d) and the other represents H or one of the values of W. The 3 $R^1$ groups are defined independently, with three $R^1$ groups drawn attached to the multi ring Ar moiety. This means that when only 1 $R^1$ represents one of the values (a)–(d) or W, the values of the other $R^1$ groups is hydrogen. It should therefore be apparent that the three $R^1$ groups can be the same or different from each other. All three can be H, W or one of the groups (a)–(d). Similarly, all three could represent one of (a)–(d), three different (a)–(d) groups, or two of the $R^1$ values can represent the same (a)–(d) group, and the third $R^1$ could represent a different (a)–(d) group.

When one of the R 1 groups represents (a)–(d), the value of $R^2$ is H or W. Likewise, when $R^2$ represents one of (a)–(d), the $R^1$ groups all represent H or W. Again, this means that all three $R^1$ groups can be H or W, or one $R^1$ can represent H or W, and the remainder of the $R^1$ groups represent the other of H and W.

Some $R^1$ and $R^2$ substituents may be distinguishable from others chemically or with respect to the biological properties which they confer. In related compounds, it has been found that the compounds afford greater water solubility and reduced potential for CNS side effects. Substituents which tend to confer improved water solubility on the overall compound have been found useful, since they are contemplated to improve the pharmacokinetics of the compound involved. Although a substantial number and range of R substituents has been described herein, all of these are contemplated to be a part of the present invention in connection with the genus of formula I.

When a group is termed "substituted", unless otherwise indicated, this means that the group contains from 1 to 3 substituents $R^q$ thereon. With respect to alkyl groups, the substituents thereon are selected from the variables specified. Preferred substituent groups include $C_{1-4}$ alkyl, $C_{2-6}$ alkenyl, $C_{2-6}$ alkynyl, hydroxy, $C_{1-4}$ alkoxy, aryl, heteroaryl, aralkyl, halo, cyano, nitro, carboxyl and the anionic function groups, as these terms are defined above.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as McOmie, J. (ed) *Protecting Groups in Organic Chemistry* pp. 46–119 (1973).

The preferred compounds of the invention include compounds where the R variable represents H, halo, alkylthio, alkylsulfonyl or cyano.

A preferred subgenus of compounds of formula I is shown below as formula Ia.

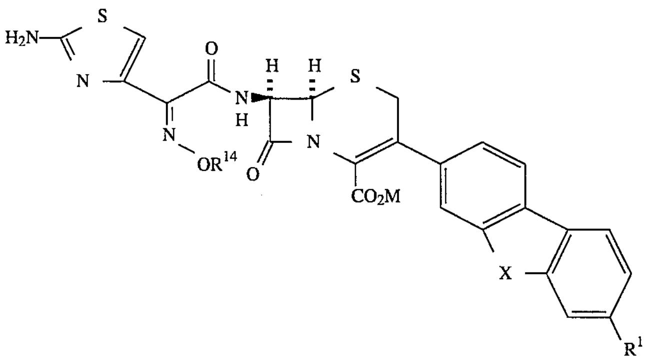

Ia with M representing hydrogen, a negative charge or a metal cation; $R^1$ representing one of groups (a)–(d), and X representing —$CH_2$—, —$CH_2CH_2$— or —C(O)—, and $R^{14}$ is equal to H or $C_{1-4}$ alkyl.

Another subgenus included in the invention is represented by formula Ib:

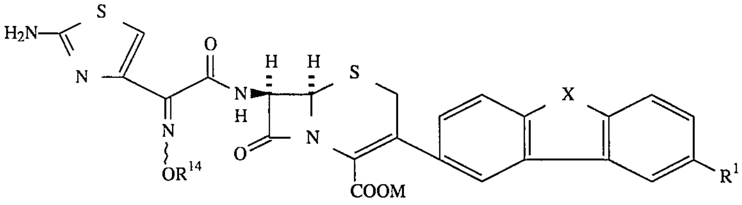

Ib with M, X and $R^1$ as described above for formula Ia, and $R^{14}$ representing H or $C_{1-4}$ alkyl. The bond indicates that the configuration-of the N bonds can be E, Z or a mixture of such isomers. All such configurations are included in the invention.

Another subgenus of compounds of the invention is represented by formula Ic:

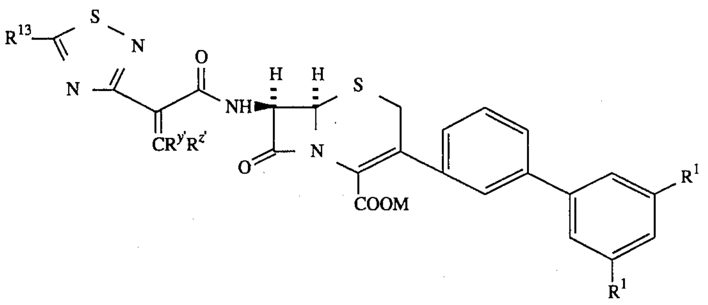

Ic wherein $R^{13}$ represents H, $NH_2$, $C_{1-4}$ alkyl, $C_{1-4}$ alkylamino or di ($C_{1-4}$ alkyl) amino; $R^{y'}$ and $R^{z'}$ independently represent H, $C_{1-6}$ alkyl, $C_{3-8}$ cycloalkyl or $C_{1-6}$ alkyl substituted with $C_{3-8}$ cycloalkyl; M represents hydrogen, a negative charge or a metal cation; one $R^1$ group represents group (a) or (b), and the other represents hydrogen.

Preferred values of type (a) include the following structures:

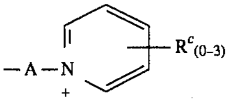

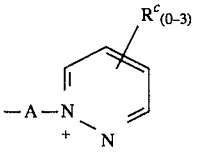

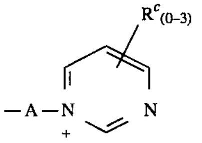

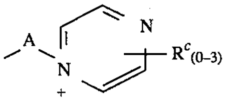

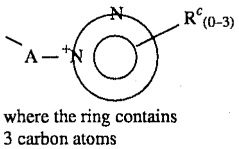

where the ring contains 3 carbon atoms

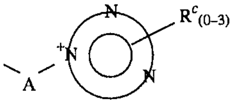

where the ring contains two carbon atoms

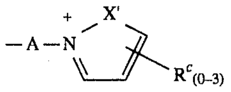

-continued

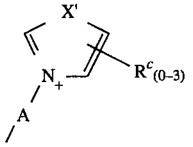

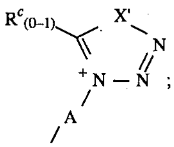

;

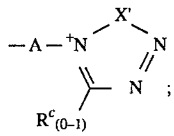

;

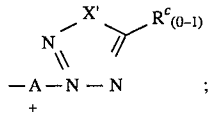

;

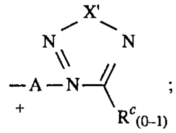

;

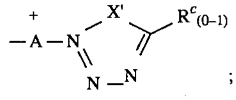

;

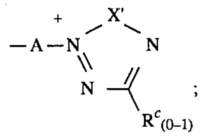

;

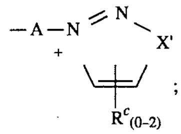

;

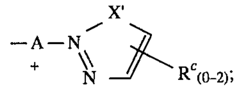

-continued

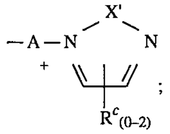

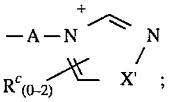

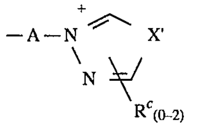

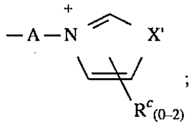

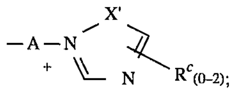

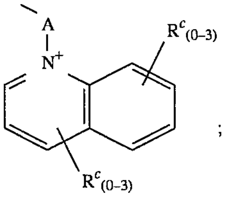

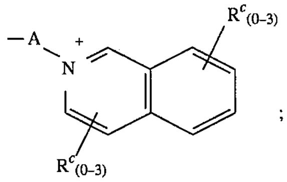

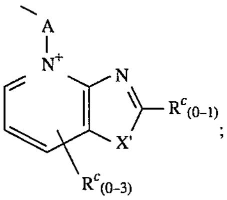

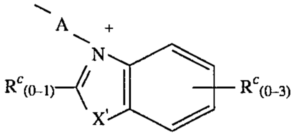

and

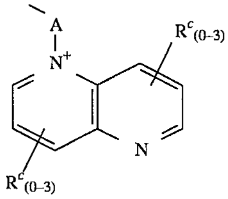

where X'=O, S, or N. Other preferred values of (a) include the structures shown above in uncharged form. In this case, the nitrogen-containing ring is partially or completely saturated.

Where $R^c$ groups are shown to have an indefinite position, they are attached to any available site of the ting. Also, in fused heterocycles, where more than one $R^c$ group is shown, this means that substitution with up to three $R^c$ groups can be present. Hence, when $R^c$ appears twice in a two ring structure, there can be up to three such $R^c$ groups in the rings.

Preferred values of type (b) include:

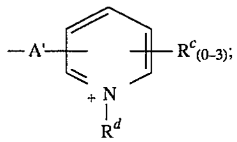

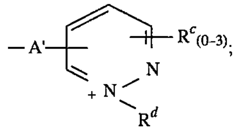

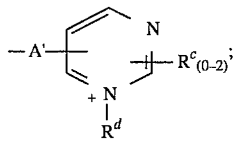

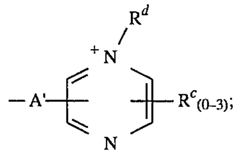

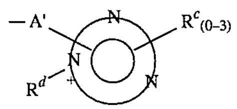

where the ring contains three carbon atoms;

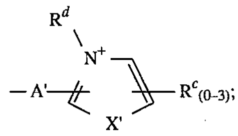

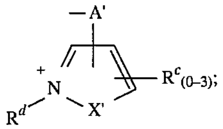

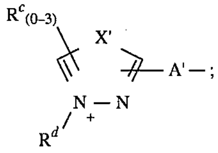

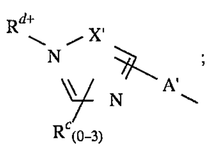

-continued

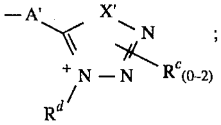
;

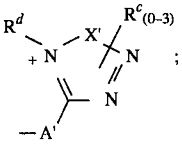
;

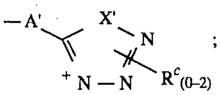
;

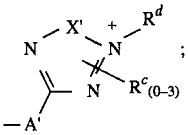
;

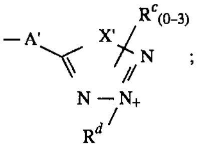
;

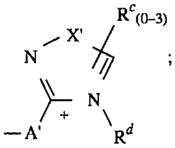
;

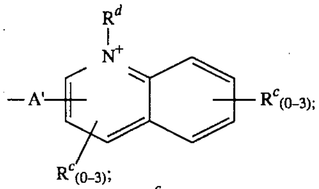

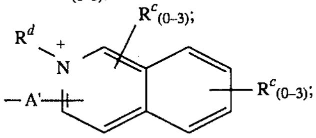

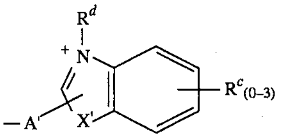

and

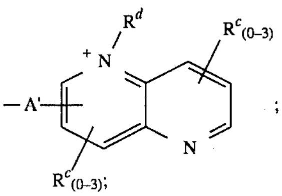
;

where X'=O or S. Other preferred values of (b) include the structures shown above in uncharged form. In each such instance, the group or groups $R^d$ are absent, or the ring is partially saturated.

For structures of type (b), where $R^c$ and/or A' are shown to have indefinite positions, they are independently attached to any available atom of the ring other than a ting nitrogen atom.

Preferred type (c) substituents include:

$—A_p—N(CH_3)_3^+$, $—A_p—N(CH_3)(CH_2CH_3)_2^+$, $—A_p—N(CH_3)_2CH_2R^{d+}$ $—A_p$13 $N(CH_2CH_3)_2CH_2CH_2R^+$,

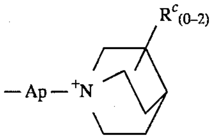

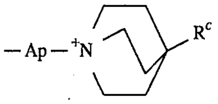

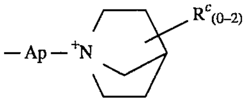

Preferred type (d) values include:

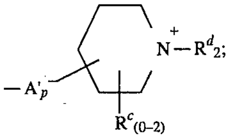

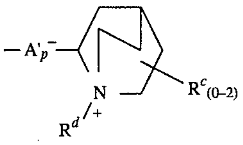

and

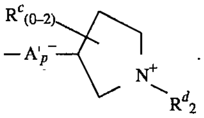

Other preferred values of (d) include the structures shown above in uncharged form. In these structures, the $R^d$ may be mono-substituted on the nitrogen atom or absent.

The scope of $R^c$ includes those groups suitable for attachment to ring carbon and nitrogen atoms. Persons skilled in the art will readily recognize that a wide range of organic substituents are suitably used as $R^c$. Persons skilled in the art will also recognize that some substituents, such as the $—NR^yR^z$ substituents, are useful carbon substitution but not equally useful for nitrogen substitution.

Preferred $R^c$ groups attached to ting carbon atoms are $—NH_2$, $—SCH_3$, $—S(O)CH_3$, $—CH_2OH$, $—(CH_2)_2OH$, $—OCH_3$, $—COOM^a$, $—CH_2COOM^a$, $—CH_2CH_2COOM^a$, $—CH_2S(O)CH_3$, $—CH_2SCH_3$, $—SO_3$ $M^a$, $—CH_2SO_3M^a$, $—CH_2CH_2SO_3M^a$, —Br, —Cl, —F, —I, $—CH_3$, $—CH_2CH_3$, $—CH_2CONH_2$ and $—CH_2C(O)N(C_1-C_4 alkyl)_2$ where $M^b$ is defined above.

Preferred $R^c$ groups attached to ring nitrogen atoms are $—CH_2OH$, $—(CH_2)_2OH$, $—CH_2COOM^a$, $—CH_2CH_2COOM^a$, $—CH_2S(O)CH_3$, $—CH_2SCH_3$, $—CH_2SO_3M^a$, $—CH_2CH_2SO_3M^a$, $—CH_3$, $—CH_2CH_3$, $—CH_2C(O)NH_2$ and $—CH_2C(O)N(C_1-C_4alkyl)_2$ where $M^a$ is defined above.

Preferred A spacer moieties include $-CH_2-$, 13 $CH_2-CH_2-$, $-CH_2-CH_2-CH_2-$, $-CH_2-CH_2-CH_2-CH_2-$, $-OCH_2CH_2$, $-S(O)CH_2-$, $-SO_2CH_2-$, $-SCH_2CH_2-$, $-S(O)CH_2CH_2-$, $-SO_2CH_2CH_2-$, $-NHCH_2CH_2-$, $-N(CH_3)CH_2CH_2-$, $-CH_2N(CH_{3)CH2}CH_2-$, $-C(O)NHCH_2CH_2-$, $-SO_2NHCH_2CH_2-$, $-C(O)CH_2-$, $-CH{=}CHCH_2-$ and $-CH_2OCH_2CH_2-$. Preferably, where Q is O, S, NH or $N(C_{1-4}alkyl)$, r plus s is 2–6.

Preferred —A'— groups include the preferred groups listed for A above. Further, A' may represent —O—, —S—, —NH—, $-SO_2-$, $-SO_2NH-$, —C(O)NH—, —CH=CH—, $-CH_2S-$, $-CH_2NH-$, $-C(O)NHCH_2-$ or $-SO_2NHCH_2-$.

When either of the $R^1$ and $R^2$ groups represents alkoxy substituted with $R^q$, the preferred $R^q$ values are —OH, $-OCH_3$, $-CF_3$ and $-CO_2M^a$. In $-COOM^a$, the preferred values of $M^a$ are H and methyl.

When $R^1$ or $R^2$ represents $-OC(O)R^s$, the preferred $R^s$ values are $C_{1-4}$ alkyl and substituted $C_{1-4}$ alkyl.

When $R^1$ or $R^2$ represents $-OC(O)NR^yR^z$, the preferred $R^y$ and $R^z$ values are H, lower alkyl and $C_{4-5}$ alkylidene.

When $R^1$ or $R^2$ represents $-S(O)_x-R^s$, x preferably is zero, and $R^s$ is preferably alkyl.

When $R^1$ or $R^2$ represents $-SO_2NR^yR^z$, $R^y$ and $R^z$ preferably represent H, lower alkyl or are taken together to represent a $C_{4-5}$ alkylidene group.

When $R^1$ or $R^2$ represents $-N(R^t)C(O)H$, $-N(R^t)C(O)-$ $C_{1-4}$ alkyl or substituted alkyl, $-N(R^t)C(O)OC_{1-4}$ alkyl or substituted alkyl, $-N(R^t)C(O)NR^yR^z$ or $-NR^tSO_2R^s$, the preferred $R^t$ groups are H and $C_{1-4}$ lower alkyl.

When $R^1$ or $R^2$ represents a $C_{5-7}$ cycloalkyl group where one carbon is replaced with a heteroatom, —NH—, O, or $-S(O)_x-$, the preferred heteroatom is nitrogen, either —NH— or $-N(C_{1-4}alkyl)-$.

When $R^1$ or $R^2$ represents an alkenyl group, the preferred alkenyl group is allyl, $-CH_2CH{=}CH_2$.

Among the more preferred $R^1$ and $R^2$ groups are $C_{1-4}$ alkyl mono-substituted with hydroxy, such as, hydroxymethyl; formyl; carbamoyl, such as, $-C(O)NH_2$; cyano; halo, such as iodo; $C_1$ to $C_4$ alkylthio, such as methylthio and its dioxide, such as $-SO_2CH_3$; and mono substituted $C_2$ to $C_4$ alkylthio, such as hydroxyethylthio, $-SCH_2CH_2OH$.

In addition to the above, examples of the more preferred $R^1$ and $R^2$ groups include:

| | |
|---|---|
| $-OCH_3$ | |
| $-OCH_2CH_2OH$ | $-OCH_2CO_2Me$ |
| —F | $-CF_3$ |
| —Br | —Cl |
| —OH | —I |
| $-OC(O)NH_2$ | $-OC(O)CH_3$ |
| $-S(O)CH_3$ | $-SCH_3$ |
| $-SCH_2CH_2OH$ | $-SO_2CH_3$ |
| $-SO_2NH_2$ | $-S(O)CH_2CH_2OH$ |
| —NHCHO | $-SO_2N(CH_3)_2$ |
| $-NHCO_2CH_3$ | $-NHC(O)CH_3$ |
| —CN | $-NHSO_2CH_3$ |
| $-C(O)CH_3$ | —CHO |
| —CH=NOH | $-COCH_2OH$ |
| $-CH{=}NOCH_2CO_2Me$ | $-CH{=}NOCH_3$ |
| $-SO_2CH_2CH_2OH$ | $-CH{=}NOCMe_2CO_2Me$ |
| $-CH{=}NOCMe_2CO_2Me$ | $-CO_2CH_2CH_2OH$ |
| $-C(O)NH_2$ | $-C(O)NHCH_3$ |
| $-C(O)N(CH_3)_2$ | $-C(O)NHCH_2CN$ |
| $-C(O)NHCH_2C(O)NH_2$ | $-C(O)NHCH_2CO_2Me$ |
| —C(O)NHOH | $-C(O)NHCH_3$ |
| -tetrazolyl | $-CO_2Me$ |

-continued

| | |
|---|---|
| $-SCF_3$ | $-PO_3HMe$ |
| $-C(O)NHSO_2Ph$ | $-C(O)NHSO_2NH_2$ |
| $-SO_3Me$ | $-SO_2NHCN$ |
| $-SO_2NHC(O)NH_2$ | —CH=CHCN |
| $-CH{=}CHCONH_2$ | $-CH{=}CHCO_2Me$ |
| $-C{\equiv}C-C(O)NH_2$ | $-C{\equiv}C-CN$ |
| $-CH_2OH$ | $-CH_2N_3$ |
| $-CH_2CO_2Me$ and | $-CH_2I$. |

The most preferred compounds of the invention include the following:

Compounds where one of $R^1$ and $R^2$ is selected from:

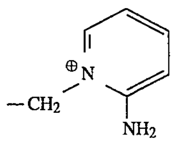

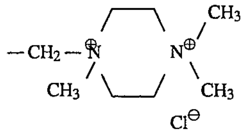

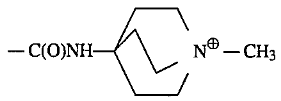

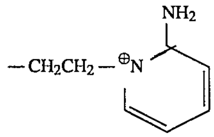

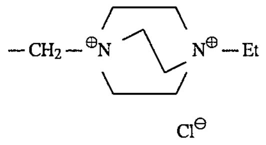

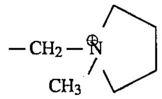

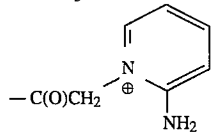

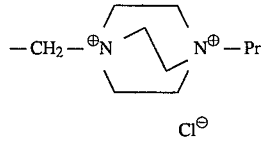

Pr = propyl
Et = ethyl

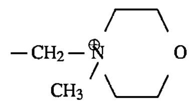

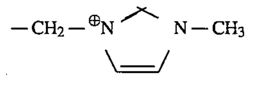

-continued

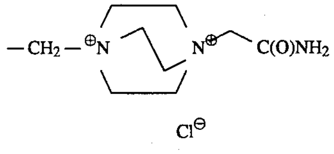

$-CH_2\overset{\oplus}{N}(CH_3)_3$

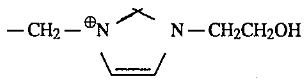

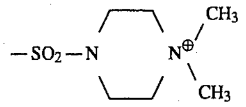

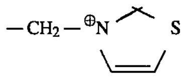

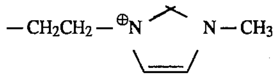

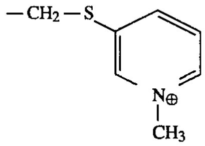

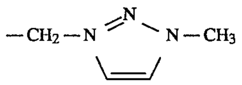

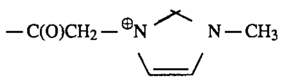

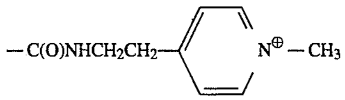

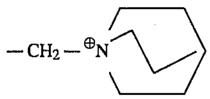

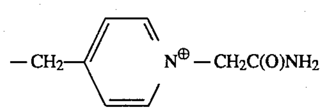

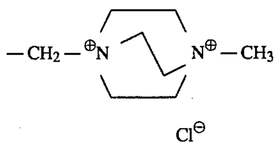

-continued

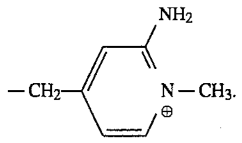

The preferred values of $R^{13}$ are H—, $NH_2$, $CH_3NH$— and $(CH_3)_2N$—.

The preferred values of Y are CH and N.

The preferred value of Y" is $N(OR^{14})$, most preferably in the Z configuration. $R^{14}$ preferably is H, $CH_3$ t-butyl or cyclopentyl.

The preferred value of Ar is the following:

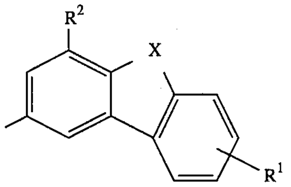

with $R^1$ and $R^2$ as described above. The preferred value of X is O, S, C(O) or absent, in which case a biphenyl group is present.

It will be recognized that the compounds of the invention can be uncharged, positively charged, negatively charged or zwitterionic, and thus electrically neutral. All such forms are included in the invention. The preferred compounds are positively charged by virtue of a positively charged nitrogen atom in group (a)–(d), and a negatively charged carboxylate group (M represents a negative charge), and a basic nitrogen in the thiazolyl ring at C-7. It is typical that when the molecule is charged, one or more counterions are present. This is the case when M represents a counterion, and is also the case when the carboxyl group is protected or in the form of a biolabile ester, and one of the groups (a) through (d) is present in positively charged form. In this case, a negatively charged counterion is present and associated with the cationic nitrogen containing group. All such forms are included in the invention described herein.

The compounds of the invention can be synthesized in accordance with the following general schemes and examples.

FLOW SHEET A
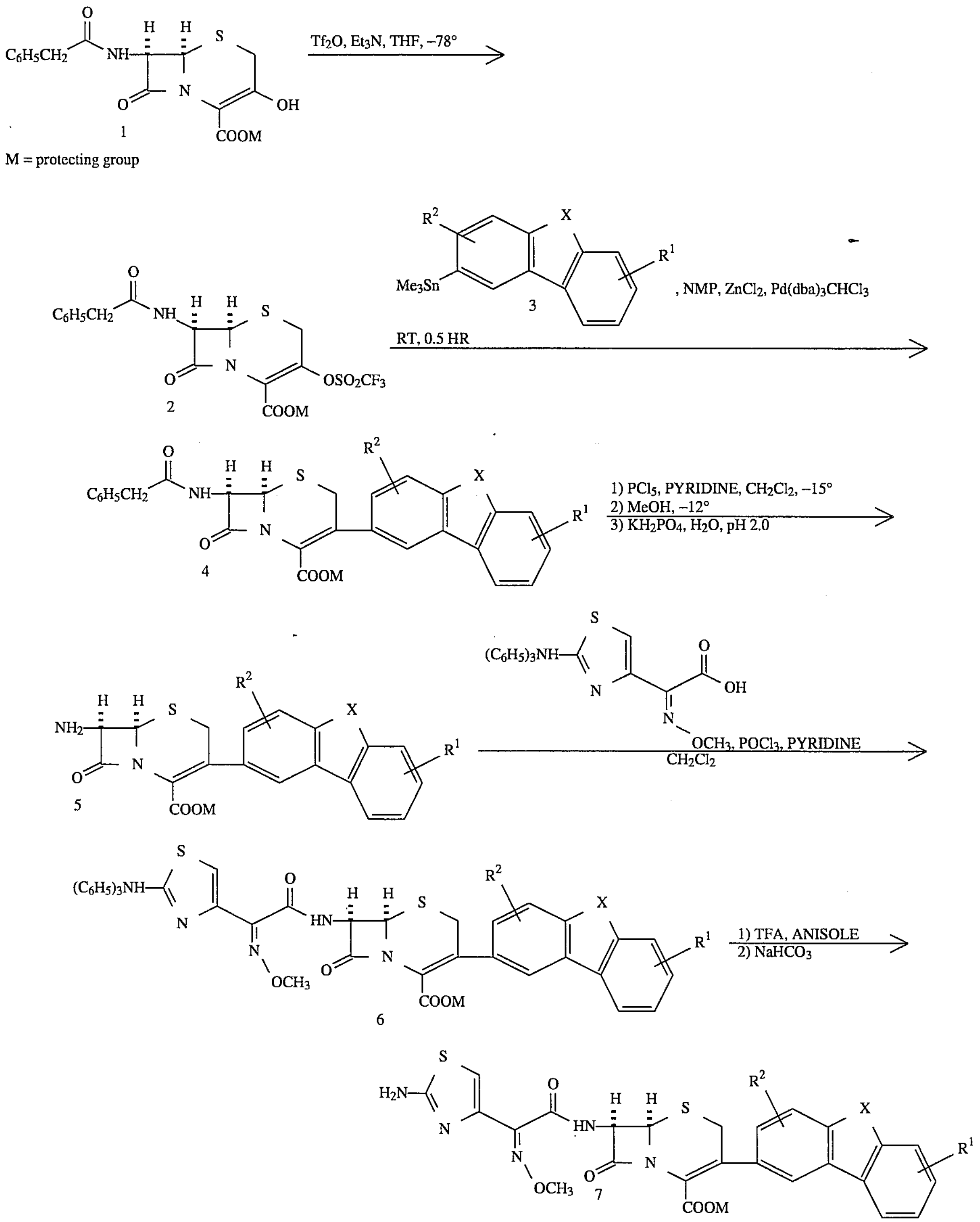
1
M = protecting group
2
3
4
5
6
7
M = $Na^+$

-continued
FLOW SHEET B

WHEN $R^1 = CH_2Cl$

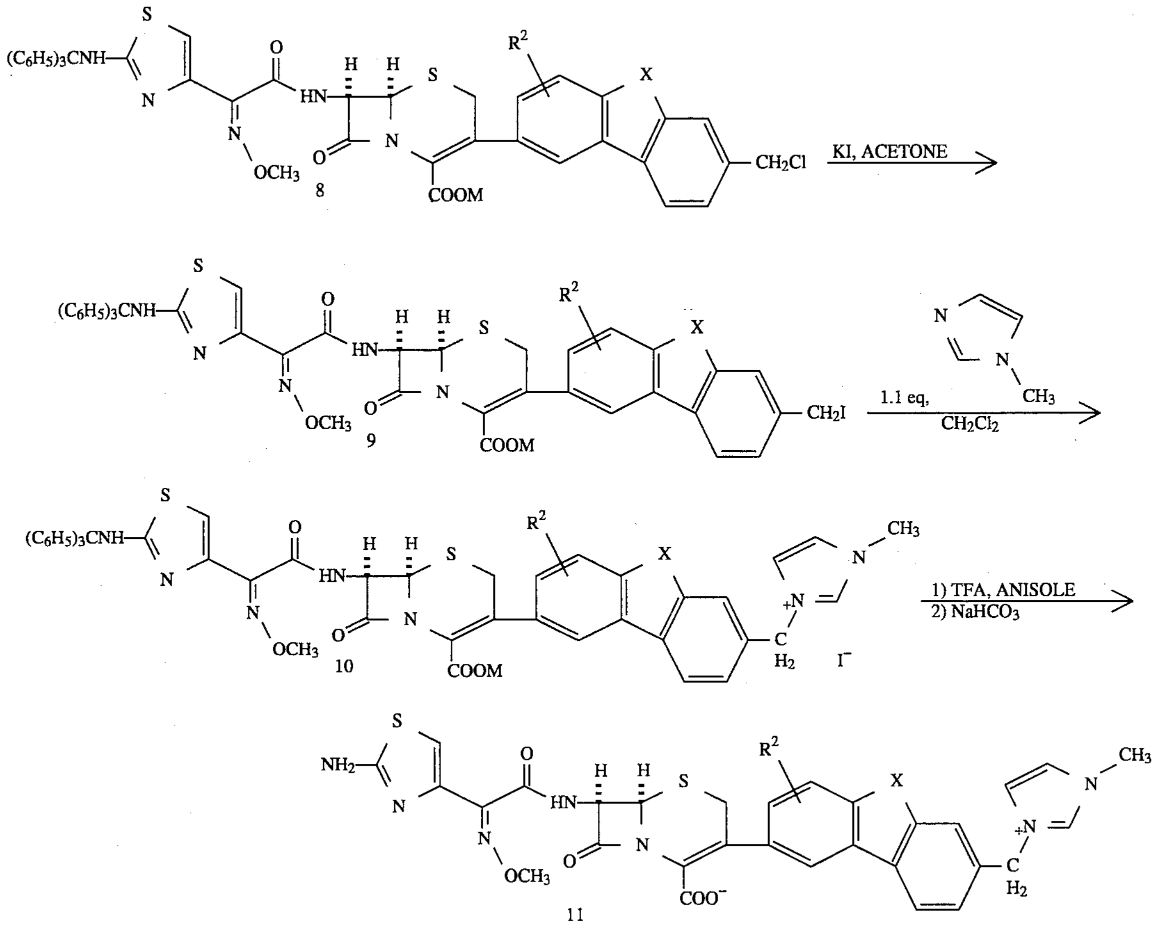

The manufacture of compounds of Formula I may be carried out as shown on flow sheet A and B. Flow sheet A shows the general synthesis of compounds which do not carry a quaternarized nitrogen bearing moiety on the aromatic substituent Ar. Flow sheet B shows the conversion of a suitably functionalized Ar substituent into a quaternarized nitrogen bearing substituent followed by removal of the protecting groups to give the desired compounds of the invention.

The starting material for the synthesis is the readily available 3-hydroxycephem 1(M=p-methoxy benzyl or benzhydryl). Reaction of 1 with a suitable trifluormethane sulfonyl source, such as trifluoromethanesulfonic anhydride, trifluoromethanesulfonic chloride or the like, in the presence of an organic nitrogen base, such as triethylamine, diisopropyl amine and the like in an aprotic solvent such as methylene chloride or tetrahydrofuran gives the trifluoromethylsulfonate at the 3-position, as a stable isolable solid 2. Reaction of 2 with a suitable aromatic stannane 3, in a polar aprotic coordinating solvent such as DMF or N-methylpyrrolidone and the like, in the presence of a palladium compound such as tris(dibenzylideneacetone)dipalladium-chloroform, palladium acetate and the like, and a phosphine such as triphenyl phosphine, tris(4-methoxyphenyl)-phosphine, tris(2,4,6-trimethoxyphenyl)phosphine and the like and in the optional presence of a metal or quaternary ammonium halide such as lithium chloride, zinc chloride or trimethyl ammonium hydrochloride, at room temperature (range 0° to 50° C.) for 10 min to 2 hours, gives the coupling product 4.

The phenylacetyl side chain at the 7-position is removed by procedures well known in the art, such as reaction with phosphorous pentachloride in the presence of a base such as pyridine at −20° to −10° C. for 1 hour, followed by reaction of the intermediate with methanol at −15° to −10° C. for 1.5 hours, followed by treatment with a phosphate buffer at pH 2 for 0.5 hour at room temperature, to give the product 5.

The free amino group at position 7 is reacylated with the desired, suitably protected acid moiety in which the carboxylic acid is activated as the acid chloride or mixed anhydride. Alternatively a coupling agent such as a carbodiimide may be used to carry out the acylation. Such acylations are well known in the art. The desired compound 6 is thus obtained.

The carboxylic acid protecting group M is then removed by treatment with a strong organic acid such as trifluoroacetic acid (TFA), in the presence of a carbonium ion acceptor such as anisole to give the free acid which is converted to the sodium salt by treatment with sodium carbonate to give 7. The procedure also results in the concomitant removal of other acid labile protecting groups in the molecule.

In the instance when the aromatic substituent at the 3-position is further substituted with a quaternary nitrogen substituent, one starts with a suitable substitution $R^1$ such as a hydroxymethyl on the aromatic stannane 3 to give compound 8, via procedures previously described. The $R^1$ substituent is converted into a leaving group by converting it to a trifluoromethane sulfonate or methanesulfonate or iodo group to give 9. Displacement of the leaving group with the nitrogen atom of a heterocyclic ring or a tertiary amine gives the quaternary nitrogen compound 10. The protecting groups are removed as described before to give the desired cephalosporin 11.

The cephalosporin compounds of the present invention are useful per se and in their pharmaceutically acceptable salt and ester forms in the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel compounds.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalare, pamoate, pectinate, persulfate, 3-phenylpropionate, picrate, pivalate, propionate, succinate, tartrate, thiocyanate, tosylate, and undecanoate.

The pharmaceutically acceptable esters of the present invention are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. The esters which are hydrolizable under physiological conditions are also referred to as "biolabile esters". Many biolabile esters have oral activity, protecting the drug from excessive acid degradation upon oral administration.

Some of the groups which M represents form biolabile esters with the carboxylate to which M is attached. Biolabile esters are biologically hydrolizable, and many are suitable for oral administration, due to good absorption through the stomach or intenstinal mucosa, resistance to gastric acid degradation and other factors. Examples of biolabile esters include compounds in which M represents an alkoxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. All of these groups can be substituted in the alkyl or aryl portions thereof with acyl or halo groups. The following species are preferred as biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-l,3-dioxolen-4-yl)methyl.

Some of the novel compounds of the present invention take the form COOM, where M is a readily removable carboxyl protecting group. Such conventional groups consist of known groups which are used to protectively block the carboxyl group during the synthesis procedures described therein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation. Examples of such ester protecting groups include benzhydryl, p-nitrobenzyl, 2-naphthylmethyl, allyl, benzyl, trichloroethyl, silyl such as trimethylsilyl or trimethylsilylethyl, phenacyl, p-methoxybenzyl, acetonyl, o-nitrobenzyl, p-methoxyphenyl, 4-pyridylmethyl and t-butyl.

The compounds of the present invention are valuable antibacterial agents active against various Gram-positive and Gram-negative bacteria, and accordingly find utility in human and veterinary medicine. The antibacterials of the invention are not limited to utility as medicaments; they may be used in all manner of industry; for example: additives to animal feed, preservation of food, disinfectants, and in other industrial systems where control of bacterial growth is desired. For example, they may be employed in compositions in concentrations ranging from about 0.01 to about 100 pans of antibiotic per million parts of solution in order to destroy or inhibit the growth of harmful bacteria on medical and dental equipment and as bactericides in industrial applications, for example in water based paints and in the white water of paper mills to inhibit the growth of harmful bacteria.

Many of compounds of the present invention are biologically active against MRSA/MRCNS. This can be demonstrated using the following biological activity protocol.

In vitro antibacterial activity determined in accordance with the protocol set forth below is predictive of in vivo activity, when the compounds are administered to a mammal infected with a susceptible bacterial organism.

Minimum inhibitory concentrations for different compounds may be calculated using the procedures set forth in Lorian, V. (ed.) *Antibiotics in Laboratory Medicine* (3rd ed.) pages 30–35 if desired. However, by comparing disc sensitivities to a known compound, e.g., imipenem, this calculation is not required to recognize MRSA/MRCNS activity.

Assay Used to Test the Activities of Compounds Against Methicillin-Resistant Staphylococci: The assay is an antibiotic disc-diffusion assay modeled after the method described-by Bauer and Kirby, et al.1, with the following modifications and clarifications:

Agar: This assay employs an agar depth of 2 mm instead of 4 mm.

Zone Readings: The inner, completely clear zone is measured.

Culture Storage: Frozen vials of strains are stored at −80° C. Working slants are prepared from frozen vials and are used for 1 month to 6 weeks. For methicillin-resistant strains the slant medium is Muleller Hinton Agar; for control strains the slant medium is Brain Heart Infusion Agar. After inoculation from frozen vials, methicillin-resistant slant cultures are incubated at 28° C. until good growth is achieved (approximately 20 hours); slants of control strains are incubated at 37° C. for 16–18 hours.

Preparation of Control Inocula for Assay: Pipet 2 ml Brain Heart Infusion Broth (BHIB) into a sterile, plastic 17×100 mm tube. Use a sterile cotton tipped applicator to pick up a very small amount of culture from the slant and twirl it in the BHIB to achieve a light but visible inoculum (approximately 1×106–107 cuf/ml). Incubate at 37° C. and 220 rpm for 17–18 hours.

Preparation of Methicillin-Resistant Inocula for Assay: For methicillin-resistant strains, inoculate 0.5 ml of BHIB heavily (to achieve appromaitely 1×108–109 cfu/ml) from the slant culture by using a sterile cotton tipped applicator. With the applicator spread approximately 0.1 ml of the suspension onto the surface of a 15×100 mm petri plate containing 10 ml Mueller Hinton Agar. Incubate the plate at 30° C. for approximately 18 hours.

Inoculum Adjustment: The 17–18 hour control Staphylococci cultures are diluted 100× in phosphate-buffered saline (PBS).

Methicillin-resistant Staphylococci: With a cotton tipped applicator, swab enough growth off the grown plates into 1 ml BHIB to achieve a visual concentration of approximately 1×109 cfu/ml. Mix vigorously and dilute in phosphate buffered saline (PBS) so that dilutions appear visually to be slightly more concentrated than the 100× diluted control cultures. Measure % transmission (% T) at 660 nm in a Spectronic 20 or other spectrophotometer. Add measured quantities of PBS to dilutions to achieve % T@1% above or below the % T measurement for the control cultures. Make sterile dilutions using the same proportions.

Plate Incubation Following Plate Inoculation and Disc Placement: Incubate control plates for 18 hours at 37° C. Incubate methicillin-resistant Staphylococci plates for 18 hours at 30° C.

The compounds of this invention may be used in a variety of pharmaceutical preparations. They may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain formulating agents. Alternatively, the active ingredient may be in powder (lyophillized or non-lyophillized) form for reconstitution at the time of delivery with a suitable vehicle, such as sterile water.

Topical applications may be formulated in hydrophobic or hydrophilic bases as ointments, creams, lotions, paints, or powders.

Oral compositions may take such forms as tablets, capsules, oral suspensions and oral solutions. The oral composions may utilize conventional formulating- agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10– 60%. The composition will generally contain from about 15 mg to about 2.5 g of the active ingredient; however, in general, it is preferable to employ a dosage amount in the range of from about 250 mg to 1000 mg. In parenteral administration, the unit dosage will typically include the pure compound in sterile water solution or in the form of a soluble powder intended for solution, which can be adjusted to neutral pH and isotonic.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four is recommended. For severe, life-threatening infections against organisms at the upper limits of sensitivity to the antibiotic, a dose of about 1000– 2000 mg three to four times daily may be recommended.

For children, a dose of about 5–25 mg/kg of body weight given 2, 3, or 4 times per day is preferred; a dose of 10 mg/kg is typically recommended.

The invention is further described in the following nonlimiting examples.

EXAMPLE 1

BENZHYDRYL 7B-PHENYLACETAMIDO-3-TRIFLUORMETHANE SULFONYLOXY-CEPH-3-EM-4-CARBOXYLATE

Benzhydryl 7β-phenylacetamido-3-hydroxy-ceph-3-em-4-carboxylate (1.0 g) was dissolved in methylene chloride (20 ml) and cooled to −78° C., under nitrogen. Triethylamine (0.420 ml, 1.1 eq) was added followed 5 minutes later by trifluoromethanesulfonic anhydride (0.410 ml, 1.1 eq). The reaction mixture was stirred at −78° C. for 20 min. and then allowed to come to room temperature rapidly. The methylene chloride was removed under reduced pressure and the solid residue was dissolved in ethyl acetate, washed with water, dried over sodium sulfate and evaporated to dryness to give the desired product as a white solid.

NMR (DMSO, 200 MHz) δ3.51 (ABq, J=12, $C_6H_5CH_2$); 3.96 (ABq, J=18, S—$CH_2$); 5.3 (d, J=5.5, C-6 H); 5.89 (d of d, J=5.5, J=8, C-7 H); 7.3–7.55 (m, Ar H); 9.25 (d, J=8, NH).

EXAMPLE 2

4'-METHOXYBENZYL 7B-PHENYLACETAMIDO-3-TRIFLUORMETHANE SULFONYLOXY-CEPH-3-EM-4-CARBOXYLATE

Starting with 4'-methoxybenzyl 7β-phenylacetamido-3-hydroxy-ceph- 3-em-4-carboxylate and following the procedure above one obtains the tittle compound as a white solid.

NMR ($CDCl_3$, 200 MHz) δ3.53 (ABq, J=16, S—$CH_2$); 3.62 (ABq, J=15, $C_6H_5CH_2$); 3.78 (s, $OCH_3$); 4.9 (d, J=5.5, C-6 H); 5.24 (ABq, J=12, $CH_2C_6H_4OCH_3$); 5.86 (d of d, J=5.5, J=8, C-7 H); 6.13 (d, J=8, NH); 7.2–7.45 (m, Ar H).

EXAMPLE 3

BENZHYDRYL 7B-PHENYLACETAMIDO-3-(7-HYDROXY METHYL- 9-FLUORENON-3-YL)-CEPH-3-EM-4-CARBOXYLATE

Benzhydryl 7β-phenylacetamido-3-trifluormethanesulfonyloxy-ceph- 3-em-4-carboxylate (1.26 g) was dissolved in N-methylpyrrolidone (NMP) and treated with 3-trimethylstannyl- 7-hydroxymethyl-9-fluorenone (0.742 g). Zinc chloride (4.0 ml, 1.0M solution in ether) was added followed by $Pd_2(dba)_3.CHCl_3$ (60 mg) and the reaction mixture was stirred under nitrogen for 45 min. The reaction mixture was diluted with ethyl acetate and washed with water five times, then with saturated sodium chloride solution and then dried over anhydrous sodium sulfate. The solvent was removed under reduced pressure and the residue was crystallized from hot ethyl acetate/hexane to give 0.844 g of the desired product in the first crop and a further 0.170 g in the second crop of crystals.

NMR (ACETONE D6, 200 MHz) 15 3.78 (ABq, J=16, $C_6H_5CH_2$); 3.97 (ABq, J=16, $_S$—$CH_2$); 4.78 (s, $CH_2Cl$); 5.36 (d, J=5.5, C-6 H); 6.05 (d of d, J=5.5, 8, C-7 H); 6.87 (s, $(C_6H_5)_2CH$); 7.37–7.55 (m, Ar H); 8.18 (d, J=8, NH).

EXAMPLE 4

4'-METHOXYBENZYL-7β-PHENYLACETAMIDO-3-(4'-HYDROXYMETHYL-BIPHENYL-3-YL)-CEPH-3-EM-4-CARBOXYLATE

4'-methoxybenzyl 7β-phenylacetamido-3-trifluormethanesulfonyloxy-ceph- 3-em-4-carboxylate (58 mg) was dissolved in NMP (1 ml) and 3-trimethystannyl-4'-hydroxymethylbiphenyl (38 mg) was added followed by $ZnCl_2$ (0.2 ml, 1M soln in ether). The reaction mixture was treated with $Pd_2(dba)_3.CHCl_3$ (5 mg) and the solution was stirred under nitrogen at room temperature for 0.5 hr. The reaction mixture was diluted with ethyl acetate and washed with water 3 times, then with saturated sodium chloride solution. The organic phase was dried over anhydrous sodium sulfate and evaporated to dryness to give the crude product (88 mg). Purification by preparative tic gave the product (45.4 mg).

NMR ($CDCl_3$, 200 MHz) δ3.62 (ABq, J=16, $C_6H_5CH_2$); 3.67 (ABq, J=18, S—$CH_2$); 3.7 (s, $OCH_3$); 4.74 (s, $CH_2OH$); 4.91 (ABq, J=12, $CH_2C_6H_4OCH_3$); 5.06 (d, J=5.5, C-6 H); 5.89 (d of d, J=5.5, J=8, C-7 H); 6.16 (d, J=8, NH); 6.5–7.9(m, Ar H).

EXAMPLE 5

BENZHYDRYL 7B-AMINO-3-(7-CHLOROMETHYL-9-FLUORENON-3-YL)-CEPH-3-EM-4-CARBOXYLATE

Benzhydryl 7β-phenylacetamido-3-(7-hydroxymethyl-9-fluorenon- 3-yl)-ceph-3-em-4-carboxylate (150 mg) was dissolved in methylene chloride (6 ml), cooled to −15° under nitrogen. Pyridine (0.240 ml was added followed by $PCl_5$ (2.4 ml, 8% solution in $CH_2Cl_2$). The reaction mixture was stirred at —15° to −10° for 65 min. The temperature was then lowered to −300 and MeOH (1.5 ml) was added drop wise and the reaction was stirred at −10° to −5° for 1.5 hrs, then at 0° for 1 hr. and then at room temperature for 1 hr. $KH_2PO_4$ (6.0 ml, 0.5M solution) was added. The reaction mixture was stirred vigorously for 0.5 hr. The organic solvents were removed under reduced pressure and the residual suspension was filtered, the residue was washed well with water and then with ether and the residue dried to give the desired product as a yellow solid( 108.3 mg).

NMR (ACETONE D6, 200 MHz) δ5 3.91 ( ABq, J=17, S—$CH_2$); 4.91(s, $CH_2Cl$); 5.42 (d, J=4.5, C-6 H); 5.76 (d, C-7 H); 6.84 (s, $(C_6H_5)_2H$); 6.0–7.8 (m,ArH).

EXAMPLE 6

BENZHYDRYL 7B-[(Z)-(2-TRITYLAMINO-A-(METHOXYLIMINO)-4-THIAZOLACETAMIDO]-3-(7-CHLOROMETHYL-9-FLUORENON-3-YL)-CEPH-3-EM-4-CARBOXYLATE (Z)-2-(tritylamino)-α-(methoxyimino)-4-thiazolacetic acid hydrochloride (25.5 mg) was suspended in $CH_2C_{12}$ (1 ml), cooled to −10° under nitrogen and treated with pyridine (9 μl). $POCl_3$ (5.2 μl) was added and the reaction mixture stirred for 20 min. to give a homogenous solution. To this was added benzhydryl 7β-amino-3-(7-chloromethyl-9-fluorenon- 3-yl)-ceph-3-em-4-carboxylate (30 mg) as a suspension in $CH_2C_{12}$, followed by pyridine (8.2 μl). The reaction mixture was allowed to warm to room temperature and stirred for 15 min. The reaction mixture was diluted with methylene chloride and washed with satd. NaCl solution dried over anhydrous sodium sulfate and evaporated to dryness to give the crude product. Purification by preparative tic gave the desired product (20.5 mg).

NMR (ACETONE D6, 200 MHz) δ3.98 ( ABq, J=20; S-$CH_2$); 3.99 (s, OCH3); 4.91 (s, $CH_2Cl$); 5.43 (d, J=5.5, C-6 H); 6.1 (d, C-7 H); 6.8–7.8 (m, ArH and $(C_6H_5)2H$); 8.52 (d, J=8, NH).

EXAMPLE 7

7 B-[(Z)-2-AMINO-A-(METHOXYLIMINO)-4-THIAZOLACETAMIDO ]-3-(7-CHLOROMETHYL-9-FLUORENON-3-YL)-CEPH- 3-EM-4-CARBOXYLIC ACID

Treatment of benzhydryl 7β-[(Z)-(2-tritylamino-α-(methoxylimino)- 4-thiazolacetamido]-3-(7-chloromethyl-9-fluorenon-3-yl)-ceph- 3-em-4-carboxylate trifluoroacetic acid in the presence of anisole gives the desired product.

EXAMPLE 8

7 B-[(Z)-2-AMINO-A-(METHOXYLIMINO)-4-THIAZOLACETAMIDO]-3-(4'-CHLOROMETHYL-BIPHENYL-3-YL)-CEPH-3-EM-4-CARBOXYLIC ACID

Starting with the product of example 4 and using the procedures described in examples 5 through 7 one obtains the desired product.

EXAMPLE 9

7B-[(Z)-2-AMINO-A-(METHOXYLIMINO)-4-(1,2,3-THIADIAZOL)-ACETAMIDO]-3-(4'-CHLOROMETHYL-BIPHENYL-3-YL)-CEPH-3-EM- 4-CARBOXYLIC ACID

Substitution of (Z)-2-(tritylamino)-α-(methoxylimino)-4-thiazolacetic acid hydrochloride by (Z)-2-(tritylamino)-α-(methoxylimino)- 4-(1,2,3-thiadiazol)acetic acid hydrochloride in the procedure of example 8 gives the desired product.

EXAMPLE 10

7B-[(Z)-2-AMINO-A-(HYDROXYLIMINO)-4-(1,2,3-THIADIAZOL)-ACETAMIDO]- 3-(4'-CHLOROMETHYL-BIPHENYL-3-YL)-CEPH-3-EM- 4-CARBOXYLIC ACID

Substitution of (Z)-2-(tritylamino)-α-(methoxylimino)-4-thiazolacetic acid hydrochloride by (Z)-2-(tritylamino)-α-(4-methoxybenzyloxylimino)- 4-(1,2,3-thiadiazol)acetic acid hydrochloride in the procedure of example 8 gives the desired product.

EXAMPLE 11

7B-[(Z)-2-AMINO-A-(CYCLOPENTYLOXYLIMINO)-4-THIAZOL-ACETAMIDO]-3-(4'-CHLOROMETHYL-BIPHENYL-3-YL)-CEPH-3-EM-4-CARBOXYLIC ACID

Substitution of (Z)-2-(tritylamino)-α-(methoxylimino)-4thiazolacetic acid hydrochloride by (Z)-2-(tritylamino)-α-(cyclopentyloxylimino)- 4-(1,2,3-thiadiazol)acetic acid hydrochloride in the procedure of example 8 gives the desired product.

EXAMPLE 12

7B-[(Z)-2-AMINO-A-(CYCLOPENTYLOXYLIMINO)-4-THIAZOL-ACETAMIDO]-3-(7-CHLOROMETHYL-9-FLUORENON-3-YL)-CEPH- 3-EM-4-CARBOXYLIC ACID

Substitution of (Z)-2-(tritylamino)-α-(methoxylimino)-4-thiazolacetic acid hydrochloride by (Z)-2-(tritylamino)-α-(cyclopentyloxylimino)- 4-thiazolacetic acid hydrochloride in the procedure of example 6, followed by the procedure of example 7 gives the desired product.

EXAMPLE 13

7B-[(Z)-2-AMINO-A-(HYDROXYLIMINO)-4-THIAZOLACETAMIDO]-3-(7-CHLOROMETHYL-9-FLUORENON-3-YL)-CEPH- 3-EM-4-CARBOXYLIC ACID

Substitution of (Z)-2-(tritylamino)-α-(methoxylimino)-4-thiazolacetic acid hydrochloride by (Z)-2-(tritylamino)-α-(4-metoxybenzyloxylimino)- 4-thiazolacetic acid hydrochloride in the procedure of example 6, followed by the procedure of example 7 gives the desired product.

EXAMPLE 14

7B-[ (Z)-2-AMINO-A-(METHOXYLIMINO)-4-(1,2,3-THIADIAZOL)-ACETAMIDO]-3-(7-CHLOROMETHYL-9-FLUORENON-3-YL)-CEPH- 3-EM-4-CARBOXYLIC ACID

Substitution of (Z)-2-(tritylamino)-α-(methoxylimino)-4-thiazolacetic acid hydrochloride by (Z)-2-(tritylamino)-α-(metoxylimino)- 4-(1,2,3-thiadiazol)-acetic acid hydrochloride in the procedure of example 6, followed by the procedure of example 7 gives the desired product.

EXAMPLE 15

7B-[ (Z)-2-(2-AMINOTHIAZOL-4-YL)-3-TERT-BUTYLMETHYLACRYLAMIDO]-3-(7-CHLOROMETHYL-9-FLUORENON-3-YL)-CEPH-3-EM-4-CARBOXYLIC ACID

Substitution of (Z)-2-(tritylamino)-α-(methoxylimino)-4-thiazolacetic acid hydrochloride by (Z)-2-(2-tritylaminothiazol-4-yl)-3-tert-butylmethylacrylic acid in the procedure of example 6, followed by the procedure of example 7 gives the desired product.

EXAMPLE 16

7 B-[(Z),2-(2-AMINOTHIAZOL-4-YL)-3-CYCLOPENTYLMETHYLACRYLAMIDO]-3-(7-CHLOROMETHYL-9-FLUORENON-3-YL)-CEPH-3-EM-4-CARBOXYLIC ACID

Substitution of (Z)-2-(tritylamino)-α-(methoxylimino)-4-thiazolacetic acid hydrochloride by (Z)-2-(2-tritylaminothiazol-4-yl)-3-cyclopentylmethylacrylic acid in the procedure of example 6, followed by the procedure of example 7 gives the desired product.

EXAMPLE 17

7B-[(Z)-2-(2-AMINOTHIAZOL-4-YL)-3-CYCLOHEXYLACRYLAMIDO]-3-(7-CHLOROMETHYL-9-FLUORENON-3-YL)-CEPH-3-EM-4-CARBOXYLIC ACID

Substitution of (Z)-2-(tritylamino)-α-(methoxylimino)-4-thiazolacetic acid hydrochloride by (Z)-2-(2-tritylaminothiazol-4-yl)-3-cyclohexylacrylic acid in the procedure of example 6, followed by the procedure of example 7 gives the desired product.

EXAMPLE 18

BENZHYDRYL 7B-[(Z)-(2-TRITYLAMINO-A-(METHOXYLIMINO)-4-THIAZOLACETAMIDO]-3-(7-IODOMETHYL-9-FLUORENON-3-YL)-CEPH-3-EM-4-CARBOXYLATE

The product of example 6 is dissolved in acetone and treated with 3 equivalents of KI. The reaction mixture is stirred at room temperature for 1 to 3 hours to give the iodo derivative.

EXAMPLE 19

BENZHYDRYL 7B-[(Z)-(2-TRITYLAMINO-A-(METHOXYLIMINO)-4-THIAZOLACETAMIDO]-3-(7-N-METHYLIMIDAZOLIUMMETHYL-9-FLUORENON-3-YL)-CEPH-3-EM-4-CARBOXYLATE

The product of example 18 is dissolved in a solvent such as methylene chloride, THF, acetonitrile or DMF and treated with 1.1 equivaent of N-methylimidazole. The reaction mixture is allowed to stir over night at room temperature. The solvent is removed at reduced pressure to give the desired product.

EXAMPLE 20

7B-[(Z)-(2-AMINO-A-(METHOXYLIMINO)-4-THIAZOLACETAMIDO] - 3-(7-N-METHYLIMIDAZOLIUMMETHYL-9-FLUORENON-3-YL)-CEPH-3-EM-4-CARBOXYLATE

The product of example 19 is treated with a mixture of trifluoroacetic acid and anisole in the ratio of 3:1 to give the desired product.

EXAMPLE 21

3-BROMO-7-METHYL-9-FLUORENONE

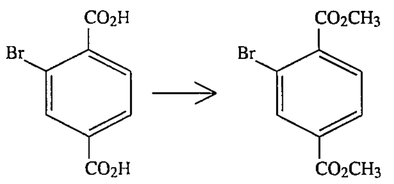

The title compound can be produced as described in U.S. Pat. No. 5,034,384.

Step A: Preparation of Dimethyl-2-bromoterphthalate

2-Bromoterphthalic acid (14.2 g) was treated with thionyl chloride (35 ml) and the reaction mixture was heated at reflux overnight. The reaction mixture was cooled and the excess $SOCl_2$ was removed under reduced pressure. The residue was treated with methanol (174 ml) at −10° C. over a one-half hour period followed by triethylamine (17.4 ml). After 15 minutes at room temperature, the methanol was removed under reduced pressure. The residue was then taken up in ethyl ether, washed with water, dried and evaporated which gave a white solid (14.65 g).

$^1$H-NMR ($CDCl_3$, 200 MHz): δ3.87 (s, $CH_3$); 7.8–8.32 (m, ArH). IR($CH_2Cl_2$, $cm^{-1}$): 1720.

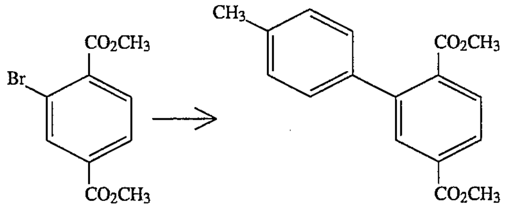

Step B: Preparation of Dimethyl-2-(4-toluyl-terphthalate

4-Bromotoluene (6 g) was dissolved in tetrahydrofuran (20 ml). To this solution at −78° C. under $N_2$ was added over a ten minute period, 1.7M tBuLi (42 ml). After two hours at room temperature, the reaction mixture was cooled to 0° C. and 1M $ZnCl_2$ (36 ml) was added over a ten minute period. After one-half hour at room temperature, bis(triphenylphosphine)nickel(H) chloride (13.2 g) was added followed by dimethyl-2-bromo-terphthalate (6 g) in tetrahydrofuran 920 ml) dropwise over a five minute period. The reaction mixture was stirred at room temperature for two hours. The tetrahydrofuran wa removed under reduced pressure. The residue was treated with ethyl acetate and 1N HCl and the layers separated. The organic phase was washed with water, brine, dried over magnesium sulfate and evaporated which gave the crude product. Chromatography on silica gel using 5% hexanes/methylene chloride gave the desired product (5.33 g).

$^1$H-NMR ($CDCl_3$, 200 MHz): δ2.42 (s, $CH_3$); 3.71, 3.96 (2s, $CH_3O$); 7.24– 8.11 (m, ArH).

IR ($CH_2Cl_2$, $cm^{-1}$): 1720.

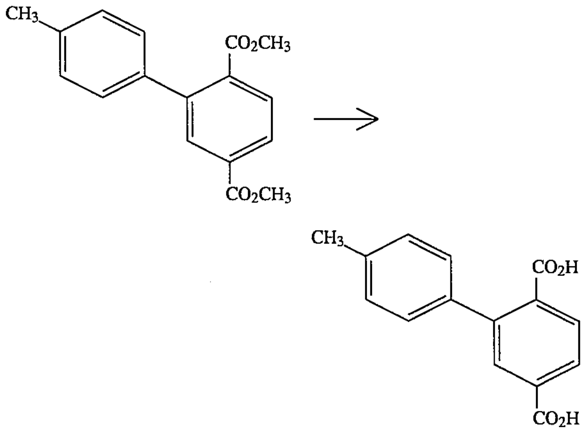

Step C: Preparation of 2-(4-toluyl)terphthalic acid

Dimethyl-2-(4-tolyl)terphthalate (11.88 g) was suspended in methanol (99 ml). 5M NaOH (50 ml) was added. The reaction mixture was heated at reflux for 1.5 hours. The methanol was removed under reduced pressure. The residue was treated with ethyl acetate and water and the layers separated. The aqueous layer was washed once with ethyl acetate. The aqueous layer was then acidified with 2N HCl and extracted three times with ethyl acetate. These combined organic extracts were then dried over $MgSO_4$, filtered and evaporated under reduced pressure which gave the product (7.09 g).

$^1$H-NMR (DMSO, 200 MHz): δ2.34 (s, $CH_3$); 7.24–8.08 (m, ArH).

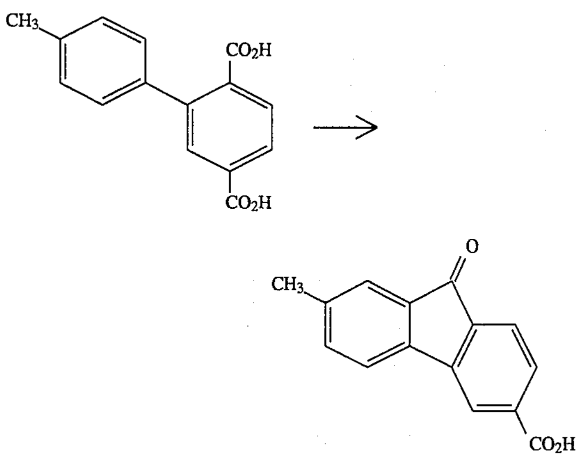

Step D: Preparation of 7-methyl-9-fluorenone-3-carboxylic acid 2-(4-tolyl)terphthalic acid (7 g) at 0° C. was suspended in concentrated H2SO4 (41 ml). The reaction mixture was heated at 40° C for four hours ( a black solution develops). Ice was added to the reaction mixture and the precipitated yellow solid was filtered, washed well with water and dried under high vaccum. The filtrate was extracted three times with ethyl acetate. The combined organic layers were dried with MgSO4, filtered and evaporated under reduced pressure which gave the desired product as a yellow solid. This was combined with the precipitated yellow solid which gave 6.5 g of the desired product.

$^1$H-NMR (DMSO, 200 MHz): δ2.33 (s, $CH_3$); 7.42–8.21 (m, ArH).

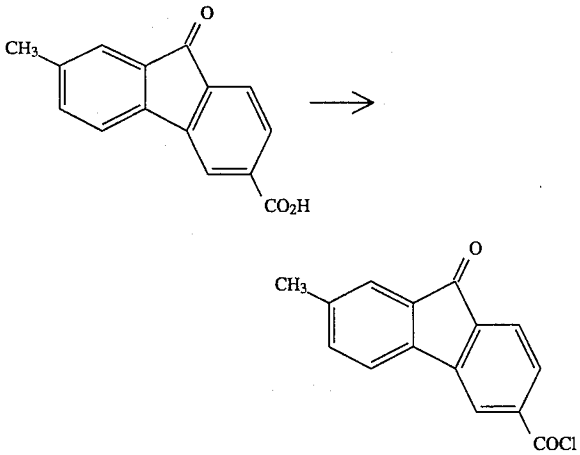

Step E: Preparation of 7-methyl-9-fluorenone-3-carboxylic acid chloride 7-methyl-9-fluorenone-3-carboxylic acid (6.5 g) was suspended in methylene chloride (110 ml) at 0° C. 2M oxalyl chloride (30 ml) was added followed by DMF (1.17 ml added over a three hour period). The reaction mixture was stirred at room temperture for twenty hours. The reaction mixture was filtered and the methylene chloride was removed under reduced pressure which gave the crude product (7.0 g).

$^1$H-NMR ($CDCl_3$, 200 MHz): δ2.42 (s, $CH_3$); 7.38–8.41 (m, ArH).

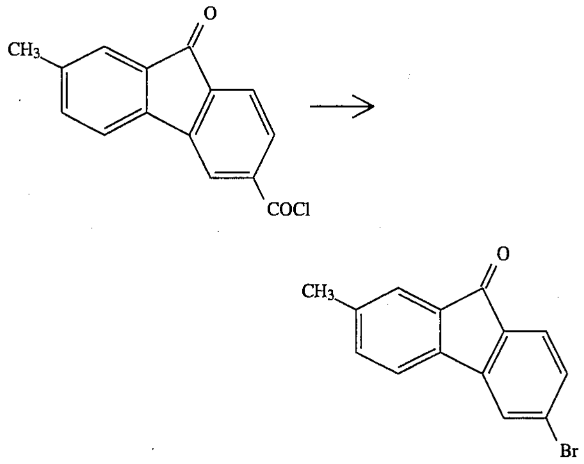

Step F: preparation of 3-Bromo-7-methyl-9-fluorenone

7-Methyl-9-fluorenone-3-carboxylic acid chloride (7 g) was dissolved in $BrCCl_3$ (130 ml), azo bis(isobutyronitrile) (AIBN) (2.33 g) in methylene chloride (20 ml) was added. This solution was then added dropwise over a 45 minute period to a suspension of the sodium salt of 2-mercaptopyridine-N-oxide (6.13 g) in $BrCCl_3$ (70 ml) at 100° C. Additional AIBN (235 mg) in a minimum of methylene chloride was then added. The reaction mixture was stirred at 100° C. for twenty minutes, diluted with methylene chloride, washed with aqueous sodium bicarbonate, dried and evaporated. The residue was chromatographed on silica gel using 50% hexanes/methylene chloride which gave the desired product (2.9 g).

H-NMR ($CDCl_3$, 200 MHz): δ2.41 (s, $CH_3$); 7.32–7.64 (m, ArH).

IR ($CH_2Cl_2$, $cm^{-1}$): 1715:

EXAMPLE 22

3-BROMO-7-HYDROXYMETHYL-9-FLUORENONE

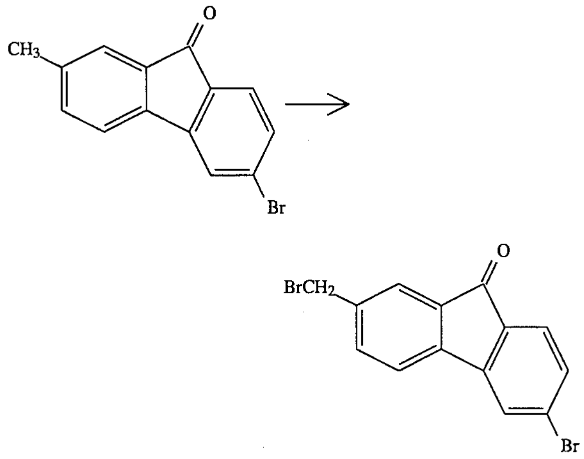

Step A: Preparation of 7-bromomethyl-3-bromo-9-fluorenone

3-Bromo-7-methyl-9-fluorenone (2.6 g) was dissolved in $CCl_4$ (70 ml). To this solution at 80° C. was added N-bromosuccinimide (NBS) (1.78 g) and AIBN (260 mg). After one-half hour, additional AIBN (520 mg) was added. At fifteen hours, additional NBS (178 mg) was added. The reaction mixture was stirred at reflux for 22.5 hours. $CCl_4$ was removed under reduced pressure. Residue was then diluted with ethyl acetate, washed twice with water, once with brine, dried and evaporated which gave the crude product. Crystallization from 50% ethyl acetate/hexanes gave the pure product (1.7 g) was well as a 1/1 mixture of 7-dibromomethyl-3-bromo-9-fluorenone and 7-bromomethyl-3-bromo-9-fluorenone (476 mg) in the mother liquors.

$^1$H-NMR ($CDCl_3$, 200 MHz): δ4.52 (s, $CH_2Br$); 7.44–7.68 .(m, ArH).

IR ($CH_2Cl_2$, $cm^{-1}$): 1720.

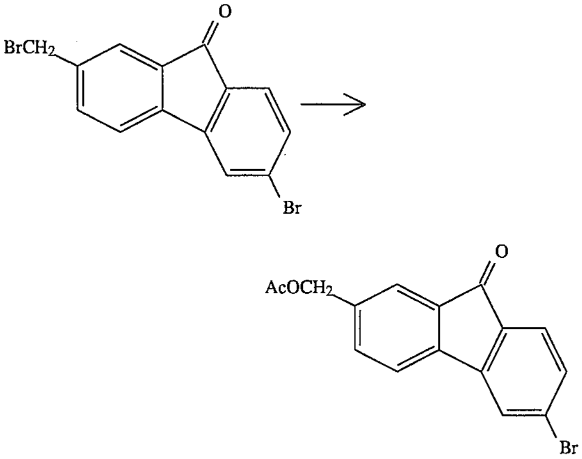

Step B: Preparation of 3-bromo-7-acetoxymethyl-9-fluorenone

7-Bromomethyl-3-bromo-9-fluorenone (1.7 g) was suspended in DMF. (25 ml). To this suspension was added potassium acetate (576 mg). The-reaction mixture was stirred at 100° C. for one hour. It was then diluted with ethyl acetate, washed four times with water, twice with brine, dried and evaporated. The residue was chromatographed on silica gel using 2% ethyl acetate/methylene chloride which gave the desired product (1.18 g).

$^1$H-NMR ($CDCl_3$, 200 MHz): δ2.12 (s, $CH_3$ —C=O); 7.42–7.68 (m, ArH).

IR ($CH_2CHl_2$, $cm^{-1}$): 1720.

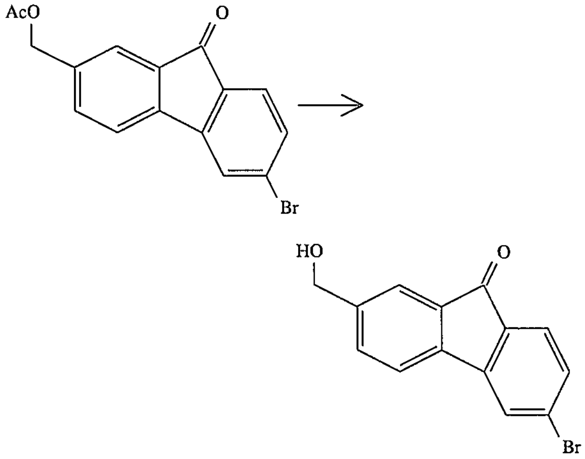

Step C: Preparation of 3-bromo-7-hydroxymethyl-9-fluorenone

3-Bromo-7-acetoxymethyl-9-fluorenone (1.18 g) was suspended in methanol (1.02 ml) and THF (23 ml). To this suspension was added 0.054 M NaOMe (6.6 ml). The reaction mixture was stirred at room temperature for 1.25 hours. It was then neutralized with 0.2M pH 7 phosphate buffer.. The tetrahydrofuran and methanol were removed under reduced pressure. The reaction mixture was then diluted with ethyl acetate, washed with water and brine, dried and evaporated which gave the product (1.0 g).

$^1$H-NMR (DMSO, 200 MHz): δ4.53 (d, J=6, $CH_2OH$); 5.35 (t, J =6, OH); 7.46–8.06 (m, ArH).

EXAMPLE 23

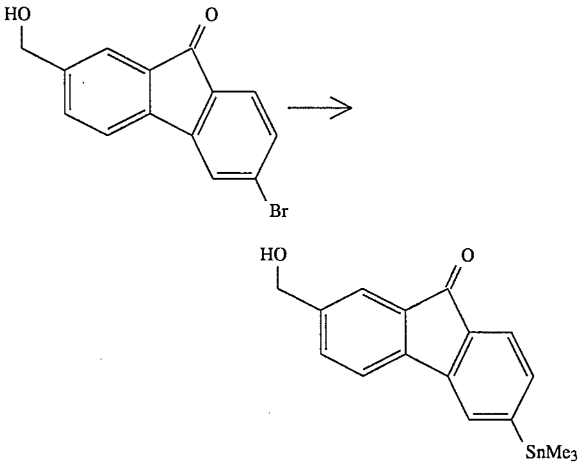

3-TRIMETHYLSTANNYL-7-HYDROXYMETHYL-9-FLUORENONE 3-bromo-7-hydroxymethyl-9-fluorenone (200 mg) was dissolved in toluene (10 ml). The reaction mixture was then degassed by bubbling in nitrogen for five minutes. To this solution at 110° C. was added hexamethylditin (282 gl) and then tetrakis(triphenylphosphine)palladium(O) (47 mg) and triphenylphosphine (3.6 mg) in toluene (10 ml) dropwise over a five minute period. The reaction mixture was stirred at 110° C for five minutes. Toluene was removed under reduced pressure. The residue was purified by preparative tlc using 20% ethyl acetate/methylene chloride which gave the desired product (205 mg).

$^1$H-NMR ($CDCl_3$, 200 MHz):δ0.36 (s, $SnMe_3$); 1.8 (t, J=6, OH); 4.73 (d, J= 6, $CH_2OH$); 7.42–7.65 (m, ArH).

IR($CH_2Cl_2$, $cm^{-1}$): 1713.

EXAMPLE 24

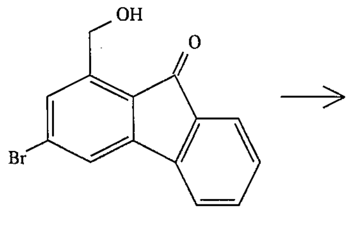

-continued

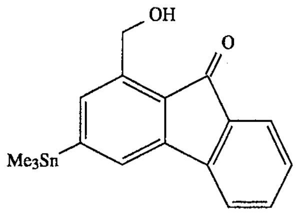

3-TRIMETHYLSTANNYL-1-HYDROXYMETHYL-9-FLUORENONE

3-Bromo-l-hydroxylmethyl-9-fluorenone (289 mg) was dissolved in toluene (4 ml) and tetrakis(triphenylphosphine-)palladium(O)( 50 mg, 0.06 eq) and triphenylphosphine (3.8 mg, 0.02 eq) were added. The solution was then degassed by bubbling in nitrogen for five minutes and then treated with hexamethyladistannane (208 μl, 1.4 eq). The reaction mixture was stirred at 110° C. under $N_2$ for 1 hour. The toluene was removed under reduced pressure and the residue was purified by preparative tlc using 20% ethyl acetate/methylene chloride which gave the desired product (230 mg).
$^1$H-NMR ($CDCl_3$, 200 MHz): δ0.35 (s, $SnMe_3$); 4.32 (t, J=8, OH); 4.85 (d, J=8, Ar-$CH_2$OH); 7.2–7.7 (m, ArH).

EXAMPLE 25

PREPARATION OF 4-AMINO-3,5-DIBROMOBENZONITRILE

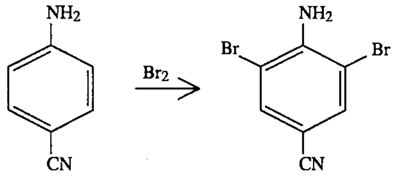

To a stirred solution of 100 mg (0.847 mmoles) of p-aminobenzonitrile in 3.6 mL dioxane chilled in an ice-bath was added sequentially 356 μL (1.78 moles) of 5N sodium hydroxide solution and mg( 1.78 mmoles) of bromine. The ice-water bath was removed and the reaction mixture was stirred further for 1.5 hours. After this time, 21.8 μL (0.423 mmoles) of bromine was added to drive the reaction to completion and stirring was continued for 10 minutes.

The mixture was partitioned between ethyl acetate and ice-water and the organic phase was separated. It was washed with brine, dried over anhydrous sodium sulfate, filtered, and evaporated.

Purification by plate layer chromatography using hexane-ethyl acetate (7:3) as the eluant provided 175 mg (74%) of the entitled product.
NMR($CDCl_3$) δ5.1 (bs, 2H), 7.66 (s, 2H).

EXAMPLE 26

PREPARATION OF 3,5-DIBROMOBENZONITRILE

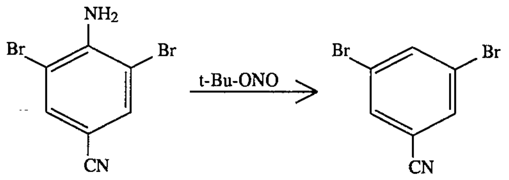

To a stirred solution of t-butylnitrite (53.5 μL, 0.449 mmoles) in 1 ml sieve dried dimethylformamide at 50° C. under an atmosphere of nitrogen was added a solution of 4-amino-3,5-dibromobenzonitrile (50 mg, 0.179 mmoles) in 1 mL of DMF. The mixture was stirred at 50° C. for 0.5 hour and partitioned between diethyl ether, ice-water, and ammonium chloride. The organic phase was separated, washed with water and brine, dried over anhydrous sodium, filtered, and evaporated.

Purification by plate layer chromatography using hexane-ethyl acetate (9:1 ) as the eluant provided 28 mg (59%) of white, crystalline product.
NMR ($CDCl_3$) δ:7.7 (d, J=1.8Hz, 2H), 7.9 (t, J=1.8Hz, 1H).

EXAMPLE 27

PREPARATION OF 4-t-BUTYLDIPHENYLSILOXYMETHYL BROMOBENZENE

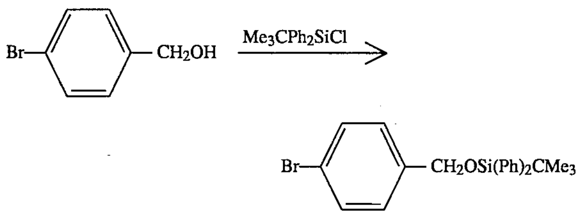

To a stirred solution of 7.48 g (40 mmoles) of p-bromobenzyl alcohol and 6.07 g (60 mmoles) of triethylamine in 70 mL of sieve dried DMF at 0° C. was added 14.3 g (52 mmoles) of neat t-butyldiphenyl-silylchloride. The ice-water bath was removed and the mixture was stirred further for 20 hours. The mixture was partitioned between ether, ice-water, and 2N hydrochloric acid, and the organic phase was separated, washed with water and brine, dried over anhydrous sodium sulfate, filtered, and evaporated.

Purification by column chromatography on 200 g of EM-60 silica gel eluting with hexanes-methylene chloride (3:1) gave 15.9 g (94%) of the title compound.
NMR ($CDCl_3$) δ1.1 (s, 9H), 4.72 (s, 2H), 7.22 (d, J=8.3 Hz, 2H), 7.43 (m, 8H), 7.7 (m, 4H).

EXAMPLE 28

PREPARATION OF 4-t-BUTYLDIPHENYLSILOXYMETHYL PHENYLBORONIC ACID

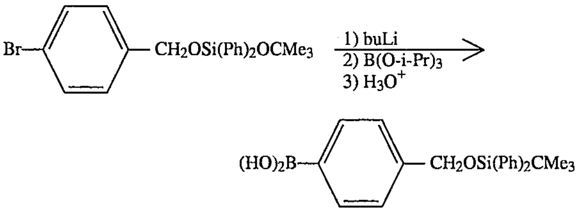

To a stirred solution of p-t-butyldiphenylsiloxymethylbromobenzene (10.1 g, 23.8 mmoles) in 100 mL of dry tetrahydrofuran at −78° under nitrogen was added dropwise 9.9 mL (25.0 mmoles) of 2.5M n-butylithium in hexane. The mixture was stirred at −78° C. for 15 minutes and 4.7 g (25.0 mmoles) of triisopropylborate was added. After 5 minutes, the low temperature bath was removed, and the mixture .was stirred further for 1.5 hours.

The mixture was poured onto ice-2N hydrochloric acid and ether was added. The biphasic mixture was stirred for 0.5 hour and the orrganic phase was separated, washed with brine, dried over anhydrous sodium sulfate, filtered and evaporated to give 8.8 g (94.2%) of crude product.

Precipitation from an ether-methylene choride solution of the crude material with hexanes gave 7.1 g (76%) from two crops.

NMR($CDCl_3$)δ:(s, 9H), 4.89 (s, 2H), 7.44 (m, 6H), 7.52 (d, J=7.8Hz, 2H), 7.74 (m, 4H), and 8.25 (d, J=7.8Hz, 2H).

EXAMPLE 29

PREPARATION OF 3-BROMO-5-CYANO-4'-t-BUTYLDIPHENYL SILYLOXYMETHYLBIPHENYL

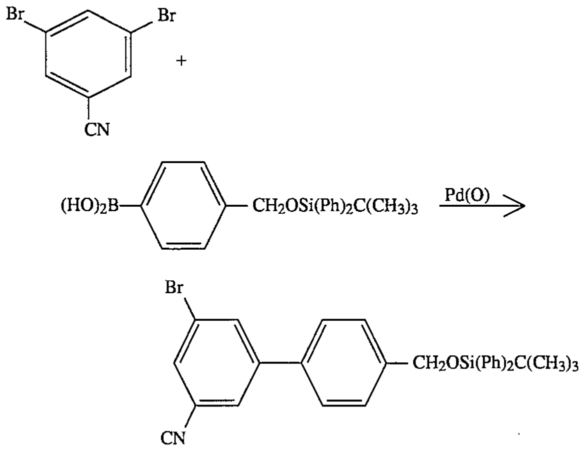

A mixture of 1.49 g (3.83 mmoles) of boronic acid derivative from Example 4, 2.0 g (7.67 mmoles) of 3,5-dibromobenzonitrile, and 133 mg (0.1 mmoles) of tetrakistriphenylphosphine in 16 mL toluene and 3.4 mL 95% ethanol with 3.47 mL (6.97 mmoles) of 2N sodium carbonate was stirred vigorously at 80° C. under nitrogen for 3.5 hours.

The mixture was partitioned between ethyl acetate and ice-water, and the organic phase was separated, washed with water and brine, dried over anhydrous sodium sulfate, filtered, and evaporated to give 2.4 g of residue.

The product can be purified by silica gel chromatography but was more conveniently purified after desilylation as described in Example 6.

NMR ($CDCl_3$) δ:1.12 (s, 9H), 4.83 (s, 2H), 7.41–7.54 (m, 10H), 7.69- 7.76 (m, 5H), 7.8 (t, J=1.6Hz, 1H), 7.96 (t, J=1.6Hz, 1H).

EXAMPLE 30

PREPARATION OF 3-BROMO-5-CYANO-4'-HYDROXYMETHYL BIPHENYL

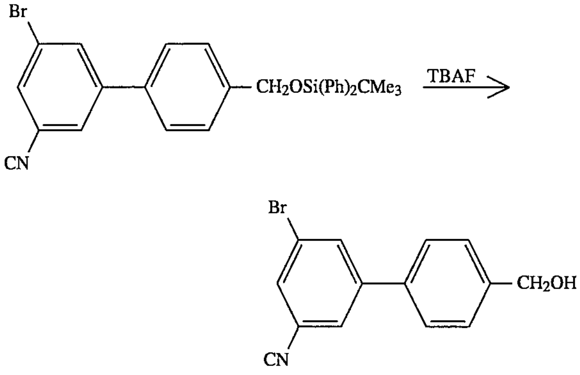

The residue 2.4 g from Example 5 was dissolved in 25 mL of dry THF and stirred while 784 μL (13.7 mmoles) of acetic acid and 4.79 mL (4.79 mmoles) of a 1M solution of tetrabutylammonium fluoride (TBAF) in THF were added. The resulting mixture was stirred at ambient temperature for 18 hours and then partitioned between ethyl acetate and ice-water. The organic phase was separated, washed with dilute sodium bicarbonate solution and brine, dried over anhydrous sodium sulfate, filtered, and evaporated.

Purification by silica gel chromatography using methylene chloride-ethyl acetate (10:1) as an eluant gave 908 mg (82% overall) of the title compound.

NMR($CDCl_3$) δ:1.73 (t, J=5.8Hz, 1H), 4.78 (d, J=5.8Hz, 2H), 7.47–7.57 (m, 4H), 7.75 (m, 1H), 7.79 (m, 1H), 7.95 (m, 1H).

EXAMPLE 31

PREPARATION OF 3-TRIMETHYLSTANNYL-5-CYANO-4'-HYDROXYMETHYLBIPHENYL

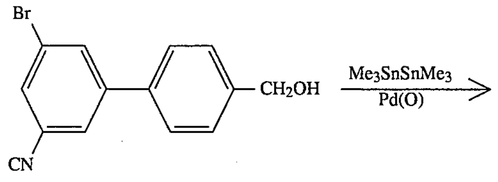

-continued

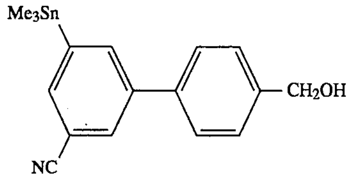

A stirred mixture of 1.76 g (6.1 mmoles) of 3-bromo-5-cyano- 4'-hydroxymethylbiphenyl, 353 mg, (0.31 mmoles) of tetrakistriphenylphosphine, 48 mg (0.18 mmoles) of triphenylphosphine and 2.4 mL (12.2 mmoles) of hexamethylditin in 17.1 mL of toluene was heated at 110° C. for 1.5 hours.

The cooled mixture was partitioned between EtOAc and ice-water and the organic phase separated, washed with water and brine, dried over anhydrous sodium sulfate, filtered and evaporated.

Purification by silica gel chromatography with methylene chloride-ethyl acetate (10:1) as eluant gave 2.21 g (93%) of the title compound, as an oil.

NMR ($CDCl_3$) δ:0.37 (s, 9H), 1.72 (t, J=5.9Hz), 4.76 (d, J=5.9Hz, 2H), 7.46–7.58 (m; 4H), 7.72 (m, 1H), 7.76 (m, 1H), 7.86 (m, 1H).

EXAMPLE 32

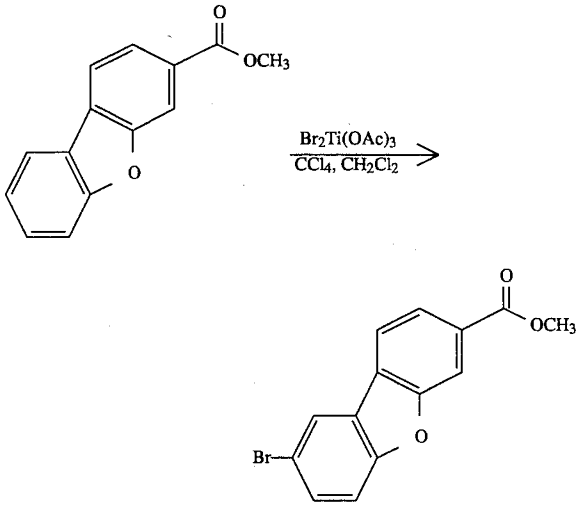

METHYL 3-BROMO-DIBENZOFURAN-7-CARBOXYLATE

To a solution of methyl dibenzofuran-2-carboxylate [0.109 g, 0.482 mmol; H. Gilman et al., J. Amer. Chem. Soc. 61, 2836 (1939)] in carbon tetrachloride (3 ml) and methylene chloride (1.5 ml) at room temperature was added thallium(III) acetate sesquihydrate (58.9 mg, 0.144 mmol). A solution of bromine (76 mg. 0.48 mmol) in 0.5 ml of carbon tetrachloride was added slowly dropwise during 1 hour. After stirring for an additional 2 hours, the mixture was filtered through 30 g of silica gel, eluting with methylene chloride. The filtrate was washed successively with $NaHSO_3$, Saturated $NaHCO_3$, $H_2O$, and brine. Drying ($MgSO_4$) and evaporatation yielded 102 mg (69%) of the title compound as a yellow solid which was used in the next step without further purification.

$^1$H-NMR (300 MHz, $CDCl_3$): δ3.98 (s, 3H, —$OCH_3$); 7.46 (d, 1H); 7.60 (dd, J=1.96, 8.73, 1H); 7.92 (d, J=8.11, 1H); 8.04–8.10 (m, 2H); 8.22 (s,. 1H).

EXAMPLE 33

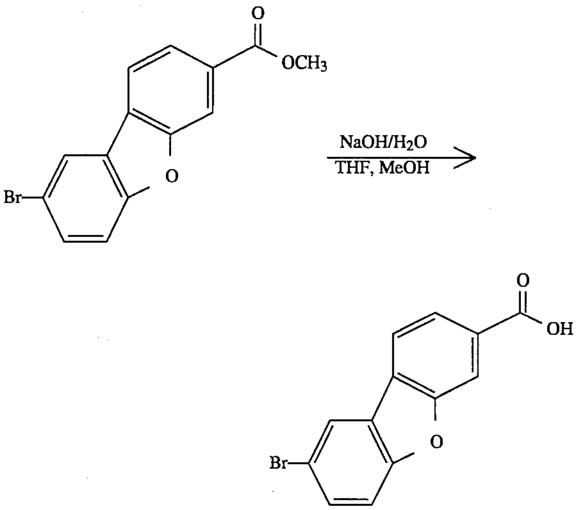

3-BROMO-DIBENZOFURAN-7-CARBOXYLIC ACID

To a mixture of methyl 3-bromo-dibenzofuran 7-carboxylate (3.2 g, 10.5 mmol) in 2:1 THF:methanol (90 ml) was added 2.5N NaOH (60 ml). After stirring at room temperature for 1 hour, the reaction was complete. Nearly all the THF:methanol was evaporated off and then the mixture was adjusted to pH=1 with concentrated HCl and extracted with ethyl acetate. Drying ($MgSO_4$) and evaporation yielded 3.1 g (100%) of the title compoundhich was used in the next reaction without purification.

$^1$H-NMR (300 MHz, $d_6$-DMSO): δ7.7–7.76 (m, 2H); 8.01 (dd, J=8.09, 1.34, 1H); 8.20 (bs, 1H); 8.30 (dd, J=8.18, 0.61, 1H); 8.54 (bs, 1H).

EXAMPLE 34

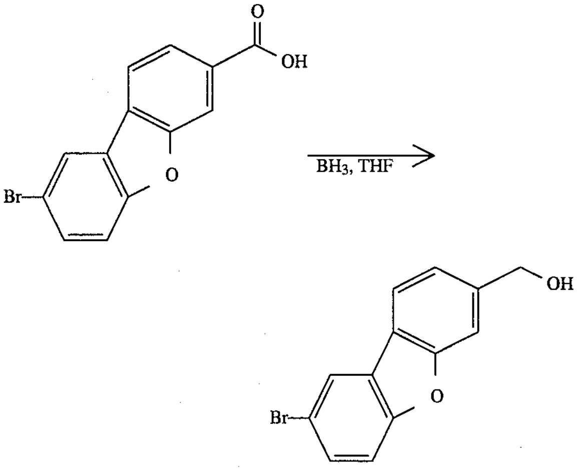

3-BROMO-7-(HYDROXYMETHYL)-DIBENZOFURAN

A cloudy solution of 3-bromo-dibenzofuran-7-carboxylic acid (3.2 g, 10.9 mmol) in 80 ml THF was cooled to 0° C. and a solution of borane in THF. (1.0M, 13.0 ml, 13.0 mmol) was added dropwise. The cooling bath was removed and the reaction was stirred at room temperature for 20 hours and was then quenched by the cautious addition of methanol (10 ml). The solution was evaporated to dryness in vacuo and the residue was dissolved in mthanol—$CH_2Cl_2$ (1:1) and again evaporated. After one repetition of this dissolution-evaporation process, 2.74 g (90%) of the title compound was obtained as a brown solid and used in the next reaction without purification.

$^1$H-NMR (300 MHz, $CDCl_3$): δ4.85 (s, 2H); 7.33 (d, J=6.96, 1H); 7.41 (d, J=8.67, 1H); 7.52 (dd, J=8.76, 2.11, 1H); 7.58 (s, 1H); 7.85 (d, J=8, 1H); 8.03 (d, j=2.02, 1H).

EXAMPLE 35

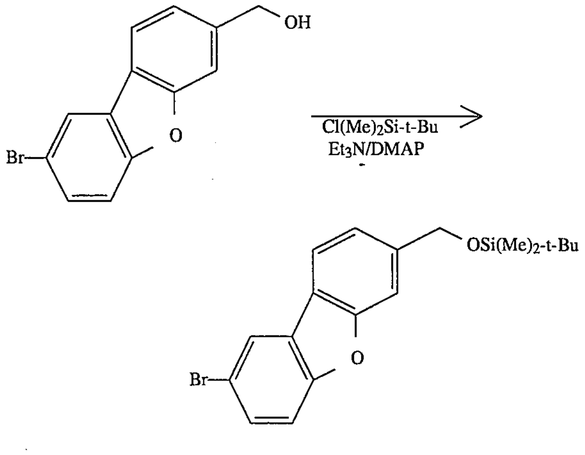

3-BROMO-7-(t-BUTYLDIMETHYLSILYLOXY METHYL)DIBENZOFURAN

To a solution of 3-bromo-7-hydroxymethyldibenzofuran (2.74 g, 9.9 mmol) and t-butyldimethylsilyl chloride (1.93 g, 12.8 mmol) in THF (60 ml) was added triethylamine (1.95 ml, 13.8 mmol) followed by 4-dimethylaminopyridine (DMAP) (120.7 mg, 0.99 mmol). After stirring at room temperature for 20 hours, the solution was poured into ethyl ether (180 ml) and washed successively with saturated $NH_4Cl$, saturated $NaHCO_3$, $H_2O$ and brine. Drying ($MgSO_4$) and evaporation gave a brown solid which was purified by flash chromatoraphy through 100 g silica gel (10% $CH_2Cl_{12}$ hexane) to yield 3.2 g (82%) of the title compound as a pale yellow solid.

$^1$H-NMR (300 MHz, $CDCl_3$): δ0.11 (s, 6H), 0.953 (s, 9H); 4.88 (s, 2H); 7.26 (d, J=8.60, 1H); 7.41 (d, J=8.67, 1H); 7.5 (dd, J=8.0, 1.89, 1H); 7.56 (s, 1H); 7.82 (d, J=8.0, 1H); 8.02 (d, J=1.96, 1H).

EXAMPLE 36

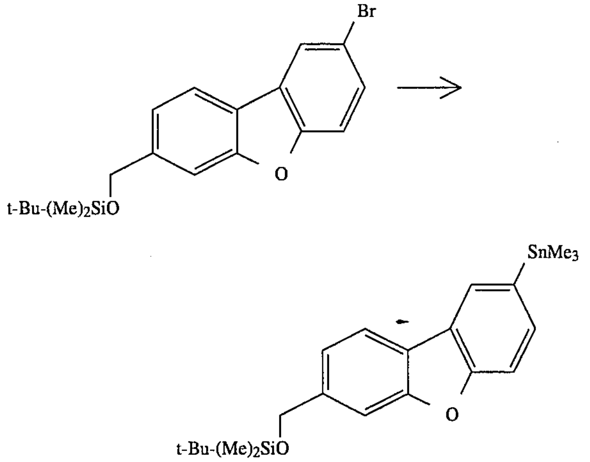

3-(TRIMETHYLSTANNYL)-7-(t-BUTYLDIMETHYL SILYLOXYMETHYL)DIBENZOFURAN

To a solution of the dibenzofuran 4 (995 mg, 2.5 mmol) in anhydrous THF (25 mL) at −78° C. under a nitrogen atmosphere was added a 1.5M t-butyllithium in pentane solution (3.0 mL, 5.25 mmol). The resulting yellow solution was stirred for 100 min., then trimethyltin chloride (548 mg, 2.75 mmol) was added as a solid. The mixture was allowed to warm to ambient temperature and then stirred for 3 hours. The reaction mixture was then poured into ether and the organic solution was washed with water (3 times) and then with brine. The organic solution was then dried with magnesium sulfate, filtered and concentrated under vacuum. Flash chromatography of the residue (silica gel, 10% methylene chloride in hexanes) provided 815 mg of the stannane (68% yield) as a crystalline solid. $^1$H-NMR (300 MHz, $CDCl_3$): δ0.22 (s, 6H), 0.35 (s, 9H), 0.95 (s, 9H) 4.88 (s, 2H), 7.24–7.28 (m, 1H), 7.52–7.59 (m, 2H), 7.89 (d, J=7.2 Hz, 1H), 8.02 ppm (s, 1H).

EXAMPLE 37

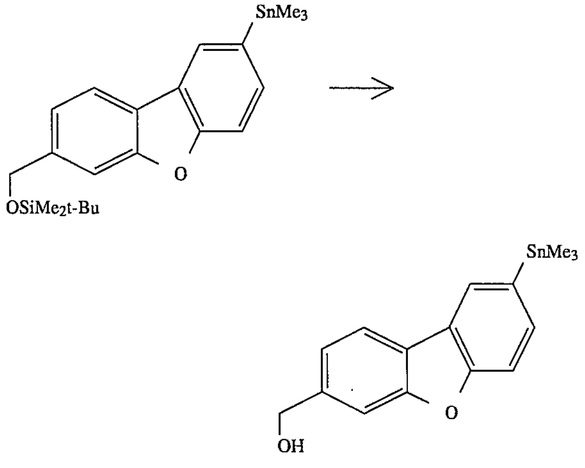

3-(TRIMETHYLSTANNYL)-7-(HYDROXYMETHYL) DIBENZOFURAN

To a solution of the dibenzofuran (339 mg, 0.71 mmol) in anhydrous THF (7 mL) at 0° C. under a nitrogen atmosphere was added dropwise a 1M solution of tetrabutylammonium fluoride in THF (0.92 mL, 0.92 mmol). The reaction solution was stirred for 30 minutes, then saturated ammonium chloride was added. The mixture was then extracted with EtOAc and the organic solution was washed with brine. The organic solution was then dried with magnesium sulfate, filtered and concentrated under vacuum. Flash chromatography of the residue (silica gel, 25% EtOAc in hexanes) provided 182 mg of the title compound (70% yield) as a white solid. $^1$H-NMR (300 MHz,$CDCl_3$): 80.35 (s, 9H), 1.75 (apparent t, J=5.0 Hz, 1H), 4.85 (d, J=5.9 Hz, 2H), 7.34 (d, J=7.8 Hz, 1H), 7.52–7.60 (m, 3H), 7.84 (d, J=7.8 Hz, 1H), 8.05 ppm (s, 1H).

EXAMPLE 38

Using the procedures set forth in Examples 1–37 and the general description, the following cephalosporins can be synthesized.

TABLE I

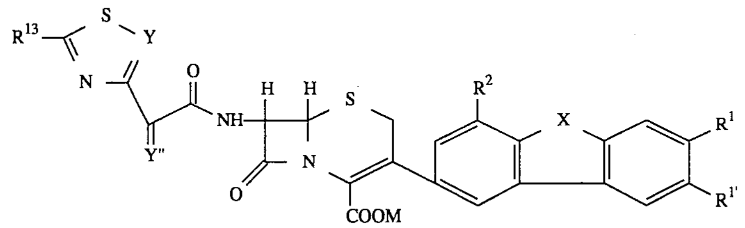

| Cpd. | Y | Y" | $R^1$ | $R^{1'}$ |
|---|---|---|---|---|
| 1 | CH | $N-OCH_3$ | H | H |
| 2 | CH | $N-OCH_3$ | $CH_2Cl$ | H |
| 3 | N | $N-OCH_3$ | $CH_2Cl$ | H |
| 4 | CH | N—OH | $CH_2Cl$ | H |
| 5 | CH | 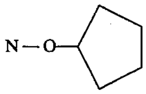 | $CH_3$ | H |
| 6 | CH | 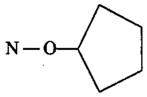 | $CH_2Cl$ | H |
| 7 | N | 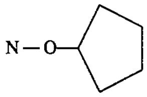 | $CH_2Cl$ | H |
| 8 | N | 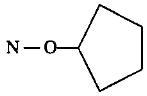 | $CH_3$ | H |
| 9 | CH | 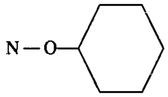 | $CH_2Cl$ | H |
| 10 | N | 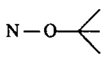 | $CH_2Cl$ | H |
| 11 | N | $N-OCH_3$ | H | $CH_2Cl$ |
| 12 | N | N—OH | H | H |
| 13 | N | $N-OCH_3$ | H | H |
| 14 | CH | $N-OCH_3$ | 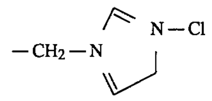 | H |
| 15 | CH | $N-OCH_3$ | 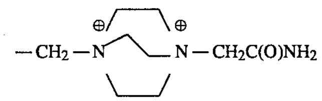 | H |

TABLE I-continued
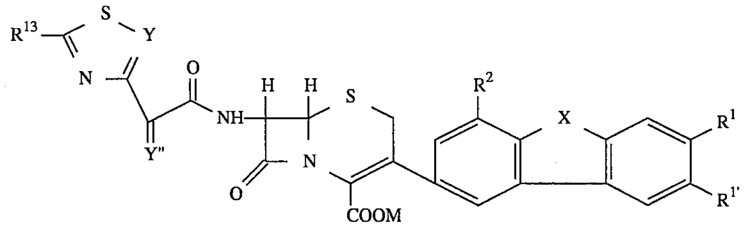
| Cpd. | Y | Y" | $R^1$ | $R^{1'}$ |
|---|---|---|---|---|
| 16 | CH | $N-OCH_3$ | 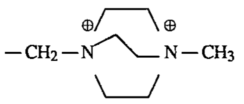 | H |
$R^{13} = NH_2$, $R^2 = H$, X = 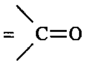
| Cpd. | Y | Y" | $R^1$ | $R^{1'}$ |
|---|---|---|---|---|
| 17 | N | $N-OCH_3$ | 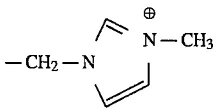 | |
| 18 | N | N—OH | 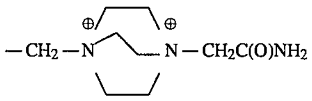 | |
| 19 | CH | N—OH | 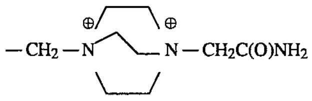 | |
| 20 | CH | 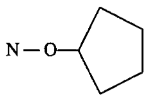 | 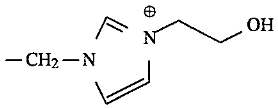 | |
| 21 | CH | 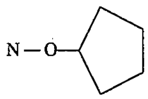 | 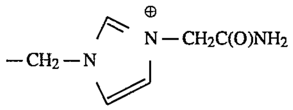 | |
| 22 | N | 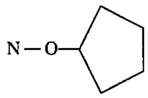 | 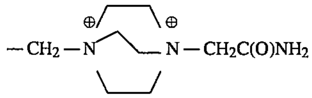 | |
| 23 | CH | $N-OCH_3$ | 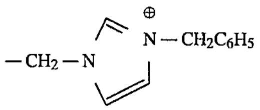 | |
| 24 | CH | $N-OCH_3$ | 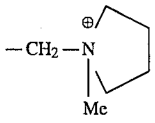 | |
| 25 | CH | $CHCH_2CH_3$ | $CH_2Cl$ | |
| 26 | N | $CHCH_2CH_3$ | $CH_2Cl$ | |
| 27 | CH | 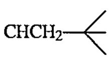 | $CH_2Cl$ | |
$R^{13} = H$, $R^2 = H$, $R^{1'} = H$, X = 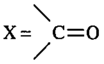

TABLE I-continued
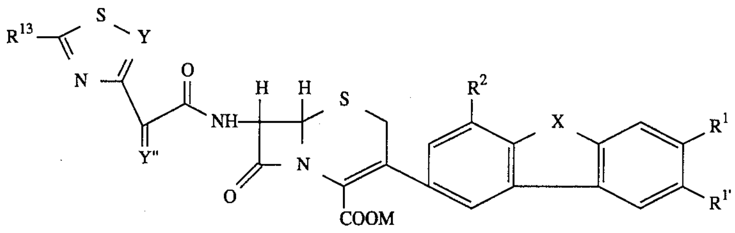
| Cpd. | Y | Y" | $R^1$ | $R^{1'}$ |
|---|---|---|---|---|
| 28 | CH | 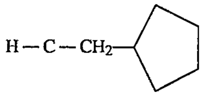 | $CH_2-Cl$ | |
| 29 | CH | 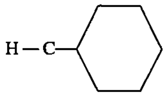 | $CH_2-Cl$ | |
| 30 | CH | $H-C-CH_2CH_3$ | 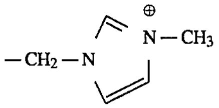 | |
| 31 | CH | 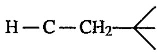 | 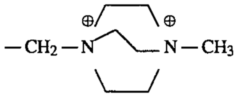 | |
| 32 | CH | 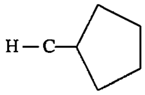 | 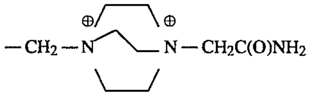 | |
| 33 | N | $H-C-CH_2CH_3$ | 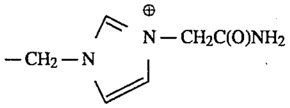 | |
| 34* | N | $H-C-CH_2CH_3$ | H | |
$R^{13} = NH_2$, $R^2 = H$, $R^1 = H$ except *, which is
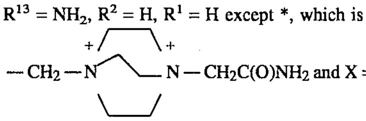 and X = 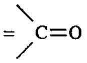
TABLE II
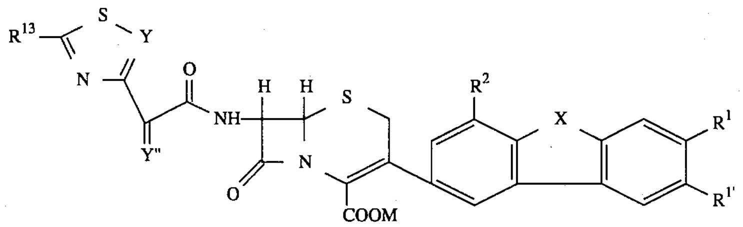
| Cpd | Y | Y" | $R^2$ | $R^1$ |
|---|---|---|---|---|
| 35 | CH | $N-OCH_3$ | H | H |
| 36 | CH | $N-OCH_3$ | $-CN$ | $CH_2Cl$ |
| 37 | N | $N-OCH_3$ | $-CN$ | $CH_2Cl$ |
| 38 | CH | $N-OH$ | H | $CH_2Cl$ |

TABLE II-continued
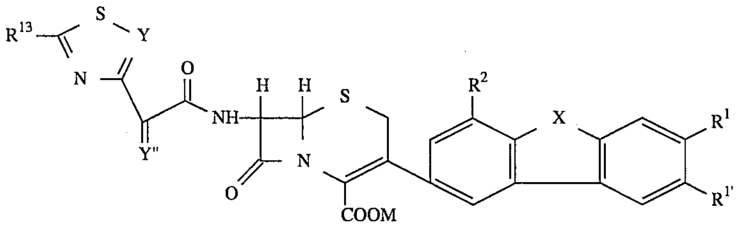
| Cpd | Y | Y" | $R^2$ | $R^1$ |
|---|---|---|---|---|
| 39 | CH | 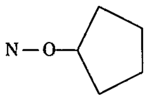 | H | $CH_3$ |
| 40 | CH | 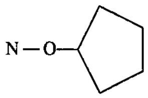 | $-CN$ | $CH_2Cl$ |
| 41 | N | 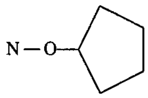 | H | $CH_2Cl$ |
| 42 | N | 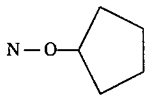 | $-CN$ | $CH_3$ |
| 43 | CH | 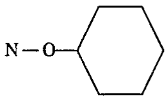 | H | $CH_2Cl$ |
| 44 | CH | 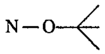 | H | $CH_2Cl$ |
| 45+ | CH | $N-OCH_3$ | $-CN$ | H |
| 46 | CH | $N-OH$ | H | H |
| 47 | N | $N-OCH_3$ | H | H |
$R^{13} = NH_2$, $R^{1'} = H$ except cpd 45+ wherein $R^{1'}$ is $CH_2Cl$
| Cpd | Y | Y" | $R^2$ | $R^1$ |
|---|---|---|---|---|
| 48 | CH | $N-OCH_3$ | H | 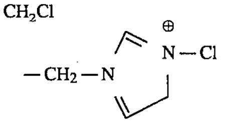 |
| 49 | CH | $N-OCH_3$ | H | 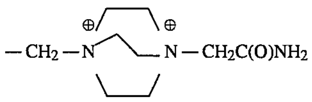 |
| 50 | CH | $N-OCH_3$ | H | 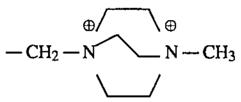 |
| 51 | CH | $N-OCH_3$ | $-CN$ | 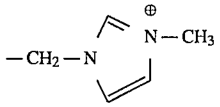 |
| 52 | N | $N-OH$ | $-CN$ | 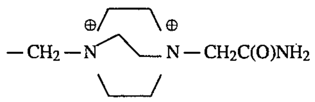 |
| 53 | CH | $N-OH$ | H | 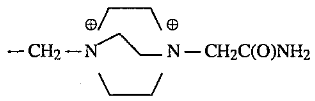 |

TABLE II-continued
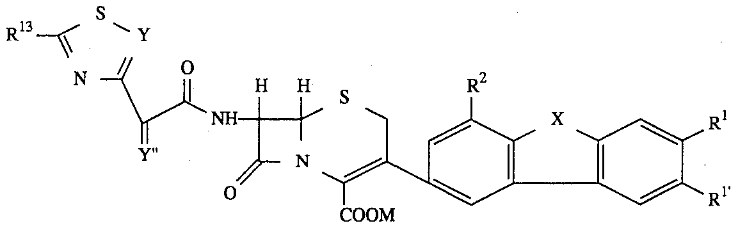
| Cpd | Y | Y" | $R^2$ | $R^1$ |
|---|---|---|---|---|
| 54 | CH | 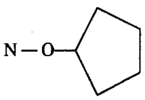 | H | 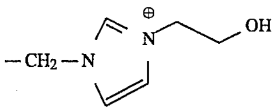 |
| 55 | CH | 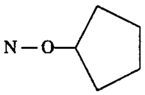 | H | 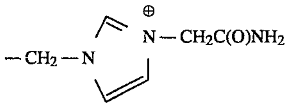 |
| 56 | N | 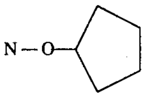 | $-CN$ | 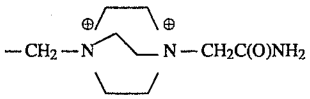 |
| 57 | CH | $N-OCH_3$ | H | 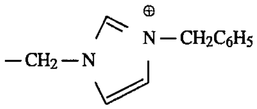 |
| $R^{13} = NH_2$, $R^{1'} = H$, X = absent | | | | |
| 58 | CH | $N-OCH$ | H | 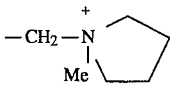 |
| 59 | CH | $CHCH_2CH_3$ | $-CN$ | $CH_2Cl$ |
| 60 | N | $CHCH_2CH_3$ | H | $CH_2Cl$ |
| 61 | CH | 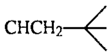 | H | $CH_2Cl$ |
| 62 | CH | 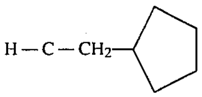 | $-CN$ | $CH_2-Cl$ |
| 63 | CH | 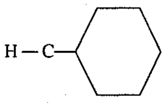 | H | $CH_2-Cl$ |
| 64 | CH | $H-C-CH_2CH_3$ | H | 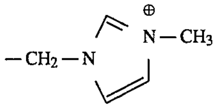 |
| 65 | CH | 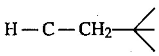 | $-CN$ | 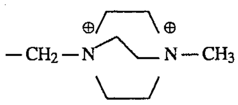 |
| 66 | CH | 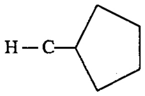 | $-CN$ | 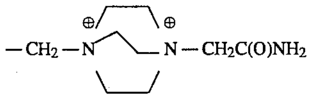 |
| 67 | N | $H-C-CH_2CH_3$ | H | 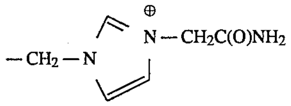 |

TABLE II-continued
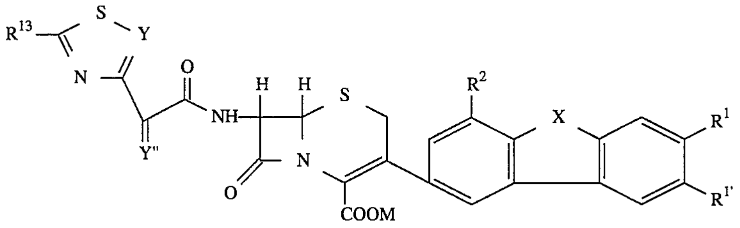
| Cpd | Y | Y'' | $R^2$ | $R^1$ |
|---|---|---|---|---|
| 68* | N | $H-C-CH_2CH_3$ | H | H |
$R^{13} = NH_2$, $R^{1'}$ = H except cpd. 68*, in which
$R^{1'}$ = 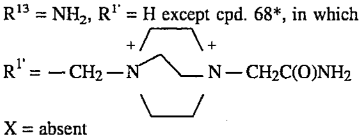
X = absent
TABLE III
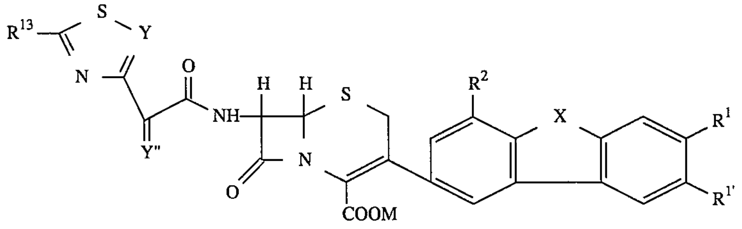
| Cpd. | Y | Y'' | $R^1$ | $R^{1'}$ |
|---|---|---|---|---|
| 69 | CH | $N-OCH_3$ | H | H |
| 70 | CH | $N-OCH_3$ | $CH_2Cl$ | H |
| 71 | N | $N-OCH_3$ | $CH_2Cl$ | H |
| 72 | CH | $N-OH$ | $CH_2Cl$ | H |
| 73 | CH | 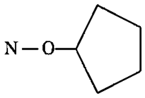 | $CH_3$ | H |
| 74 | CH | 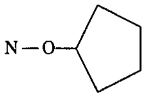 | $CH_2Cl$ | H |
| 75 | N | 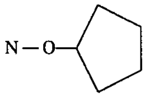 | $CH_2Cl$ | H |
| 76 | N | 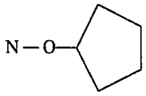 | $CH_3$ | H |
| 77 | CH | 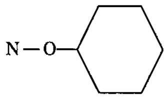 | $CH_2Cl$ | H |
| 78 | CH | 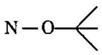 | $CH_2Cl$ | H |
| 79 | CH | $N-OCH_3$ | H | $CH_2Cl$ |
| 80 | CH | $N-OH$ | H | H |

TABLE III-continued
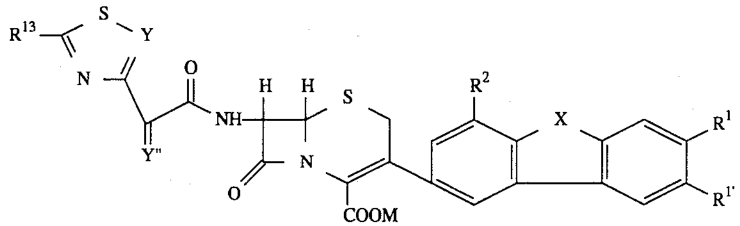
| Cpd. | Y | Y" | $R^1$ | $R^{1'}$ |
|---|---|---|---|---|
| 81 | N | $N-OCH_3$ | H | H |
| $R^{13} = NH_2$, $R^2 = H$, X = O | | | | |
| 82 | CH | $N-OCH_3$ | 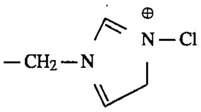 | |
| 83 | CH | $N-OCH_3$ | 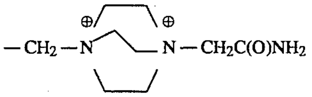 | |
| 84 | CH | $N-OCH_3$ | 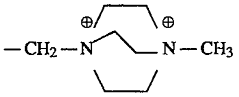 | |
| 85 | N | $N-OCH_3$ | 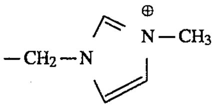 | |
| 86 | N | $N-OH$ | 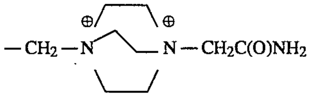 | |
| 87 | CH | $N-OH$ | 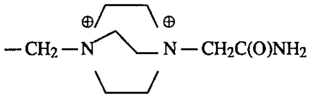 | |
| 88 | CH | 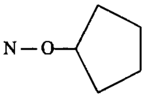 | 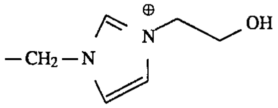 | |
| 89 | CH | 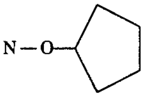 | 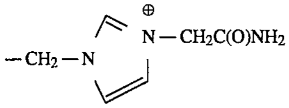 | |
| 90 | N | 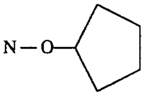 | 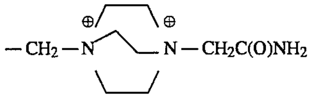 | |
| 91 | CH | $N-OCH_3$ | 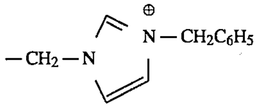 | |
| 92 | CH | $N-OCH_3$ | 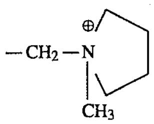 | |
| $R^{13} = NH_2$, $R^2 = H$, $R^{1'}$ H, X = O | | | | |
| 93 | CH | $CHCH_2CH_3$ | $CH_2Cl$ | |
| 94 | N | $CHCH_2CH_3$ | $CH_2Cl$ | |

TABLE III-continued
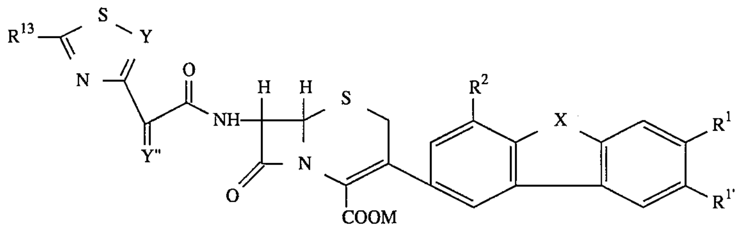
| Cpd. | Y | Y" | $R^1$ | $R^{1'}$ |
|---|---|---|---|---|
| 95 | CH | 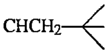 | $CH_2Cl$ | |
| 96 | CH | 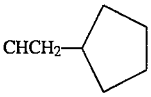 | $CH_2-Cl$ | |
| 97 | CH | 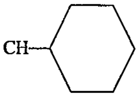 | $CH_2-Cl$ | |
| 98 | CH | $CHCH_2CH_3$ | 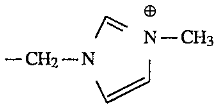 | |
| 99 | CH | 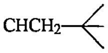 | 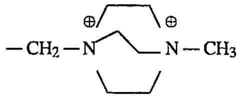 | |
| 100 | CH | 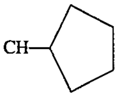 | 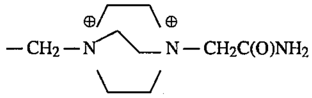 | |
| 101 | N | $CHCH_2CH_3$ | 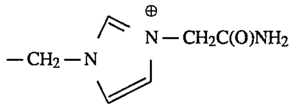 | |
| 102* | N | $CHCH_2CH_3$ | H | |
$R^{13} = NH_2$, $R^2 = H$, $R^{1'}$ H except Cpd. 102*,
where $R^{1'}$ = 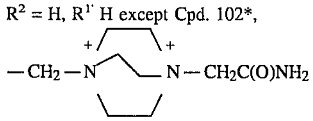
TABLE IV
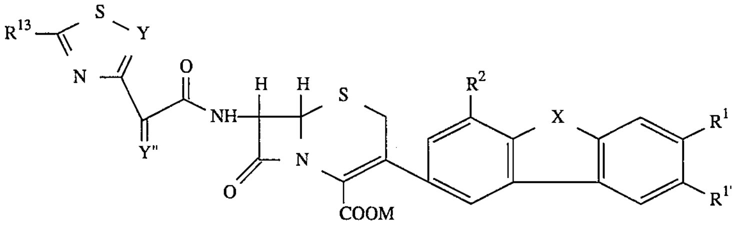
| Cpd. | Y | Y" | $R^1$ | $R^{1'}$ |
|---|---|---|---|---|
| 103 | CH | $N-OCH_3$ | H | H |

TABLE IV-continued
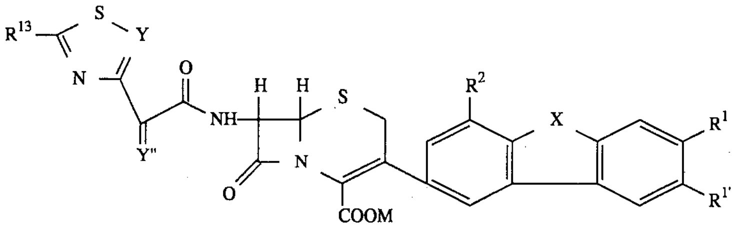
| Cpd. | Y | Y" | $R^1$ | $R^{1'}$ |
|---|---|---|---|---|
| 104 | CH | N—$OCH_3$ | $CH_2Cl$ | H |
| 105 | N | N—$OCH_3$ | $CH_2Cl$ | H |
| 106 | CH | N—OH | $CH_2Cl$ | H |
| 107 | CH | 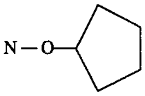 | $CH_3$ | H |
| 108 | CH | 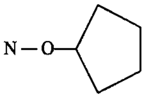 | $CH_2Cl$ | H |
| 109 | N | 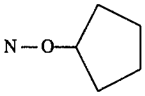 | $CH_2Cl$ | H |
| 110 | N | 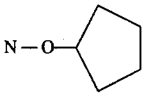 | $CH_3$ | H |
| 111 | CH | 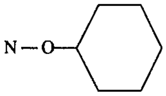 | $CH_2Cl$ | H |
| 112 | CH | 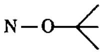 | $CH_2Cl$ | H |
| 113 | CH | N—$OCH_3$ | H | $CH_2Cl$ |
| 114 | CH | N—OH | H | H |
| 115 | N | N—$OCH_3$ | H | H |
| $R^{13} = NH_2$, $R^2$ = H, X = S | | | | |
| 116 | CH | N—$OCH_3$ | 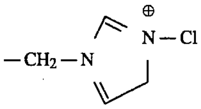 | |
| 117 | CH | N—$OCH_3$ | 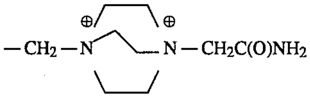 | |
| 118 | CH | N—$OCH_3$ | 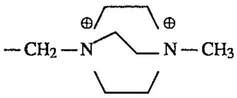 | |
| 119 | N | N—$OCH_3$ | 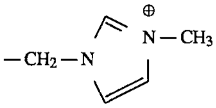 | |
| 120 | N | N—OH | 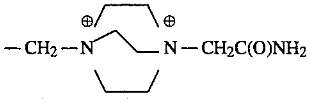 | |

TABLE IV-continued
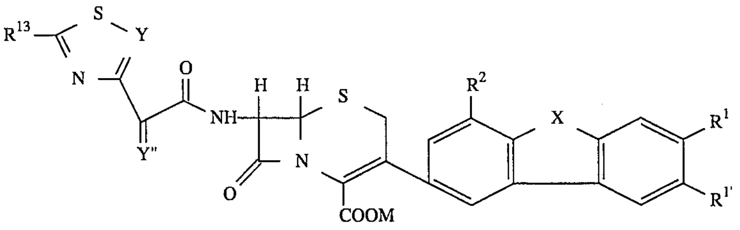
| Cpd. | Y | Y'' | $R^1$ | $R^{1'}$ |
|---|---|---|---|---|
| 121 | CH | N—OH | 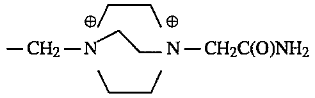 | |
| 122 | CH | 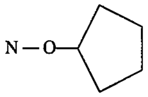 | 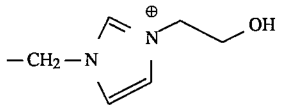 | |
| 123 | CH | 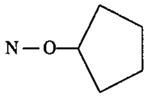 | 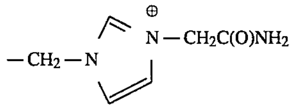 | |
| 124 | N | 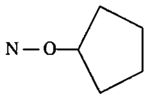 | 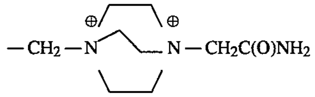 | |
| 125 | CH | N—$OCH_3$ | 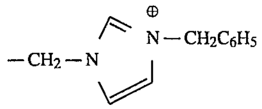 | |
| 126 | CH | N—$OCH_3$ | 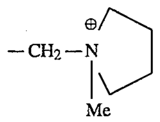 | |
| $R^{13} = NH_2$, $R^2 = H$, $R^{1'} = H$, X = S | | | | |
| 127 | CH | $CHCH_2CH_3$ | $CH_2Cl$ | |
| 128 | N | $CHCH_2CH_3$ | $CH_2Cl$ | |
| 129 | CH | 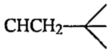 | $CH_2Cl$ | |
| 130 | CH | 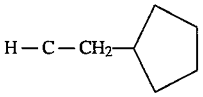 | $CH_2$—Cl | |
| 131 | CH | 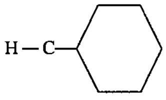 | $CH_2$—Cl | |
| 132 | CH | H—C—$CH_2CH_3$ | 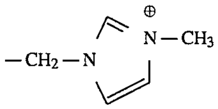 | |
| 133 | CH | 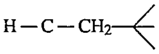 | 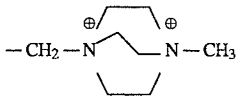 | |
| 134 | CH | 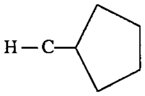 | 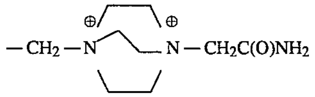 | |

TABLE IV-continued
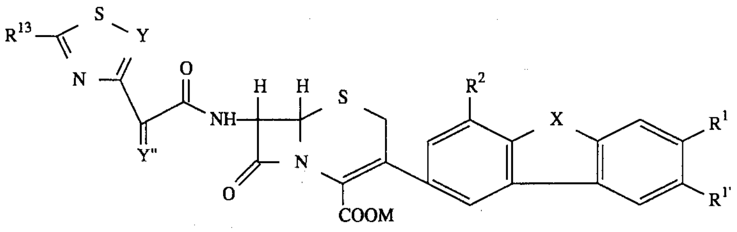
| Cpd. | Y | Y" | $R^1$ | $R^{1'}$ |
|---|---|---|---|---|
| 135 | N | H—C—$CH_2CH_3$ | 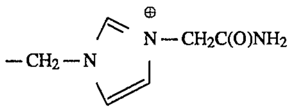 | |
| 136* | N | H—C—$CH_2CH_3$ | H | |
$R^{13} = NH_2$, $R^2 = H$, $R^{1'} = H$ except Cpd. 136*,
which is 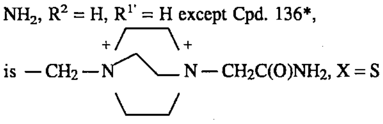, X = S
TABLE V
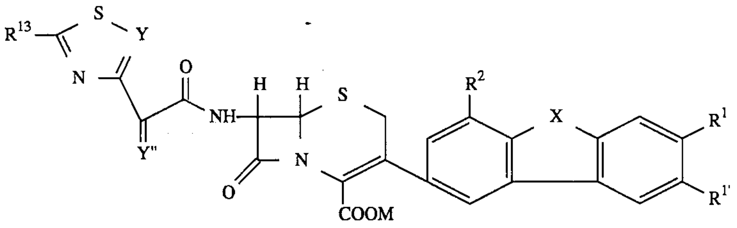
| Cpd. | Y | Y" | $R^1$ | X |
|---|---|---|---|---|
| 137 | CH | N—$OCH_3$ | H | —S(O)— |
| 138 | CH | N—$OCH_3$ | $CH_2Cl$ | —S(O)— |
| 139 | N | N—$OCH_3$ | $CH_2Cl$ | —S(O)— |
| 140 | CH | N—OH | $CH_2Cl$ | —S(O)— |
| 141 | CH | 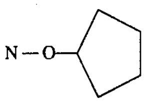 | $CH_3$ | —C=N— |
| 142 | CH | 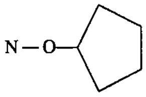 | $CH_2Cl$ | —C=N— |
| 143 | N | 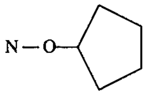 | $CH_2Cl$ | —C=N— |
| 144 | N | 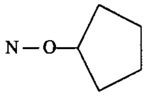 | $CH_3$ | —S(O)— |
| 145 | CH | 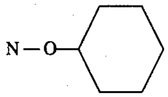 | $CH_2Cl$ | —S(O)— |

TABLE V-continued
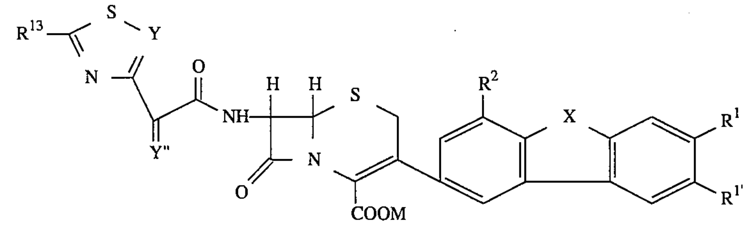
| Cpd. | Y | Y" | $R^1$ | X |
|---|---|---|---|---|
| 146 | CH | 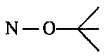 | $CH_2Cl$ | —S(O)— |
| 147** | CH | $N-OCH_3$ | H | —S(O)— |
$R^{13} = NH_2$, $R^{1'}$ = H, except Cpd. 147**, which is $CH_2Cl$.
| Cpd. | Y | Y" | $R^1$ | X |
|---|---|---|---|---|
| 148 | CH | N—OH | H | —S(O)— |
| 149 | N | $N-OCH_3$ | H | —C=N— |
| 150 | CH | $N-OCH_3$ | 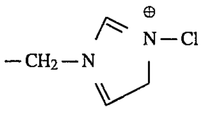 | —S(O)— |
| 151 | CH | $N-OCH_3$ | 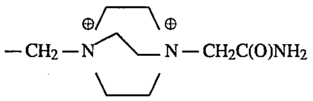 | —S(O)— |
| 152 | CH | $N-OCH_3$ | 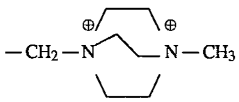 | —S(O)— |
| 153 | N | $N-OCH_3$ | 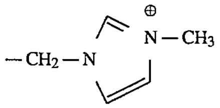 | —S(O)— |
| 154 | N | N—OH | 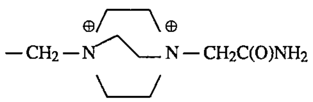 | —S(O)— |
| 155 | CH | N—OH | 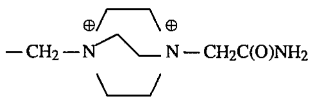 | —S(O)— |
| 156 | CH | 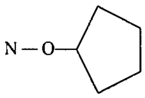 | 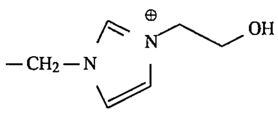 | —C=N— |
| 157 | CH | 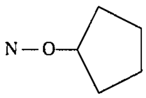 | 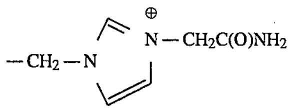 | —C=N— |
| 158 | N | 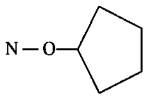 | 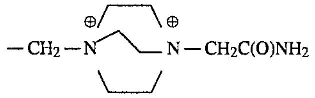 | —S(O)— |
| 159 | CH | $N-OCH_3$ | 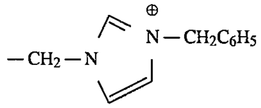 | —S(O)— |

TABLE V-continued
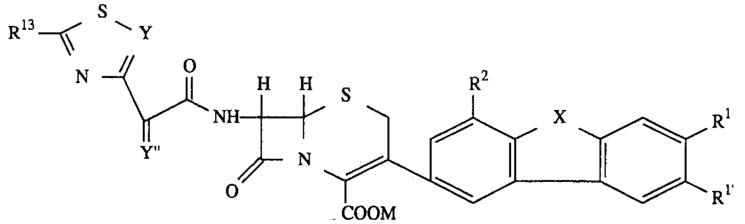
| Cpd. | Y | Y'' | $R^1$ | X |
|---|---|---|---|---|
| 160 | CH | N—$OCH_3$ | 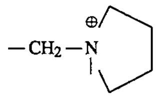 | —S(O)— |
| $R^{13} = NH_2$, $R^2 = H$, $R^{1'} = H$ | | | | |
| 161 | CH | H—C—$CH_2CH_3$ | $CH_2Cl$ | —S(O)— |
| 162 | N | H—C—$CH_2CH_3$ | $CH_2Cl$ | —S(O)— |
| 163 | CH | 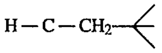 | $CH_2Cl$ | —S(O)— |
| 164 | CH | 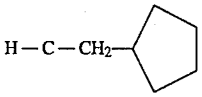 | $CH_2$—Cl | —S(O)— |
| 165 | CH | 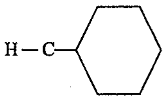 | $CH_2$—Cl | —S(O)— |
| 166 | CH | H—C—$CH_2CH_3$ | 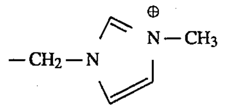 | —S(O)— |
| 167 | CH | 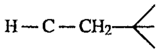 | 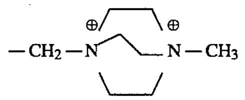 | —S(O)— |
| 168 | CH | 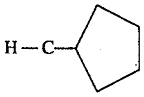 | 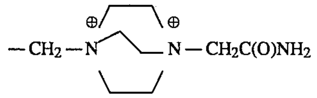 | —S(O)— |
| 169 | N | H—C—$CH_2CH_3$ | 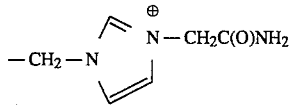 | —S(O)— |
| 170* | N | H—C—$CH_2CH_3$ | H | —S(O)— |
$R^{13} = NH_2$, $R^2 = H$, $R^{1'} = H$ except Cpd. 170*,
which is 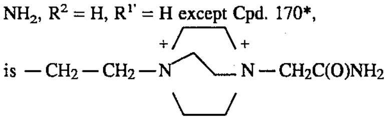
What is claimed is:
1. A compound of the formula I:
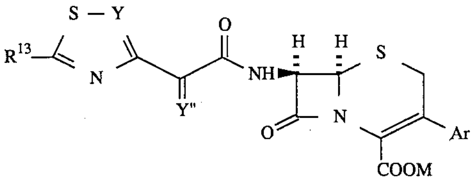

or a pharmaceutically acceptable salt or solvate thereof, wherein:

$R^{13}$ represents hydrogen, $NH_2$, C1–4 alkyl, C1–4 alkylamino or di(C1- 4)alkylamino-;

Y represents CH or N;

Y" represents (a) $CR^{y'}R^{z'}$, with $R^{y'}$ and $R^{z'}$ independently representing H, $C_{1-6}$ alkyl, $C_{3-8}$ cycloalkyl or $C_{1-6}$ alkyl substituted with $C_{3-8}$ cycloalkyl, or (b) N substituted with $—OR^{14}$ with $R^{14}$ representing H, $C_{1-4}$ alkyl, $C_{3-6}$ cycloalkyl or $C_{1-4}$ alkyl substituted with COOH;

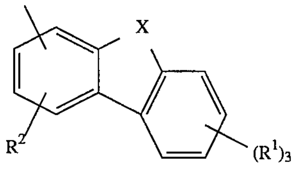

wherein X is either present or absent; when present, X represents $—CH_2—$, $—CH_2CH_2—$;

one of $R^1$ and $R^2$ represents hydrogen, W as defined below or one of the groups (a) through (d) below, and the other represents H or W with the proviso that each $R^1$ group is considered independently;

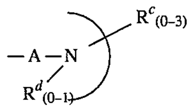
(a)

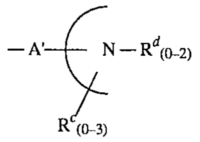
(b)

$—Ap—NR^{10}R^{11}R^{12}{}_{(0-1)}$; (c)

and

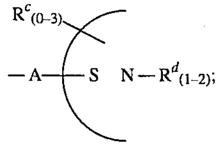
(d)

when one of $R^1$ and $R^2$ represents (a)

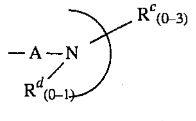

A represents $—(CR^{3'}R^{4'})_r—Q—(CR^{3'}R^{4'})_s—$ wherein r represents an integer of from 0–6, s represents an integer of from 1–6 and Q represents: a covalent bond, —O—, —S(O)x— with x equal to 0, 1 or 2,$—NR^{3'}—$, $SO2NR^{3'}—$, $—NR^{3'}SO_2—$, $—C(O)NR^{3'}—$, $—NR^{3'}C(O)—$, $—CR^{3'}=CR^{4'}—$, —C(O)— or —OC(O)—;

with $R^{3'}$ and $R^{4'}$ independently representing H or C1–4 lower alkyl, and $(CR^{3'}R4')_s$- being attached to the ring nitrogen;

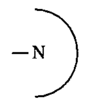

represents a 5 or 6 membered monocyclic heterocycle or an 8–10 membered bicyclic heterocycle, bonded to A through the ting nitrogen and having a substituent group $R^d$ optionally attached to the ring nitrogen, and having 0–3 $R^c$ groups attached to other atoms of the heterocyclic group, said ring nitrogen being tertiary or quaternary by virtue of the ring bonds and $R^d$ which may be optionally attached, said heterocyclic group being saturated or unsaturated, aromatic, partially aromatic or non-aromatic, said heterocycle also containing 0–3 additional nitrogen atoms and 0- 1 oxygen or sulfur atom;

each $R^c$ independently represents W as defined below or $NR^yR^z$, wherein $R^y$ and $R^z$ independently represent H, C1 to C4 alkyl, C1 to C4 alkyl substituted with $R^q$, or $R^y$ and $R^z$ are taken together to represent either a 3- to 5- membered alkylidene radical to form a ring, optionally substituted with $R^q$, or a 2- to 4- membered alkylidene radical interrupted by O or S(O)x with x equal to 0, 1 or 2, to form a ring, said alkylidene being optionally substituted with $R^q$ as defined below;

each $R^d$ independently represents hydrogen, $NH_2$, O— or C1 to C4 alkyl, optionally mono-substituted with $R^q$ as defined below;

$R^q$ is selected from hydroxy, methoxy, cyano, $—C(O)NH_2$, $—OC(O)NH_2$, —CHO, $—OC(O)N(CH_3)_2$, $—SO_2NH_2$, $—SO_2N(CH_3)_2$, $—S(O)CH_3$, $—SO_2CH_3$, —F, $—CF_3$, $—SO_3M^b$ with $M^b$ representing H or alkali metal, or $—CO_2M^a$, where $M^a$ is H, alkali metal, methyl or phenyl; tetrazolyl (where the point of attachment is the carbon atom of the tetrazole ting and one 6f the nitrogen atoms is optionally mono-substituted by another $R^q$ group as defined above);

when one $R^1$ and $R^2$ represents (b)

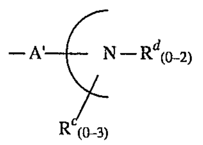

A' represents $—(CR^{3'}R^{4'})_{m'}$ $—Q—(CR^{3'}R^{4'})_{m'}—$ with each m' independently equal to 0–6, and Q, $R^{3'}$ and $R^{4'}$ are as defined above, except that when each m' is O, Q is not a covalent bond, and $—(CR^{3'}R^{4'})_{m'}$ is attached to the phenyl ting;

represents a 5 or 6 membered monocyclic heterocycle or an 8–10 membered bicyclic heterocycle, said heterocycle being unsaturated and aromatic, partially aromatic or non-aromatic, bonded to A' through an atom other than the ring nitrogen, and optionally having 0–2 $R^d$ substituent groups attached to the ring nitrogen, said nitrogen in the heterocycle being tertiary or quaternary by virtue of the ring bonds and the optional $R^d$ groups which may be attached;

said heterocycle may further contain 0–1 oxygen or sulfur atom and 0–2 additional nitrogen atoms therein;

$R^c$ and $R^d$ are as defined above;

when one of $R^1$ and $R^2$ represents (c) $—A_p—NR^{10}R^{11}R^{12}$ (0–1 );

A is as defined above and p is an integer 0 or 1;

$R^{10}$, $R^{11}$ and where present, $R^{12}$, are independently H, C1–4 alkyl or C1–4 alkyl optionally mono-substituted with $R^q$;

or $R^{10}$, $R^{11}$ and $R^{12}$ may be taken in combination to represent a C4 to C10 alkanetriyl group, optionally substituted with up to three W groups, with W as defined below;

such that the nitrogen atom to which said $R^{10}$, $R^{11}$ and $R^{12}$ groups are attached is tertiary or quaternary;

when one of $R^1$ and $R^2$ represents (d)

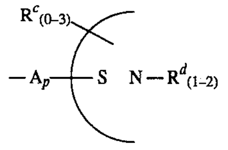

A, p, $R^c$ and $R^d$ are as previously defined, and

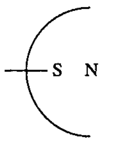

represents a saturated 5 or 6 membered monocyclic heterocycle or an 8–10 membered bicyclic heterocycle, bonded to A' through an atom other than the ring nitrogen, and having one or two $R^d$ substituent groups attached to the ring nitrogen, said nitrogen in the heterocycle being tertiary or quaternary by virtue of the ring bonds and the $R^d$ groups which may be attached;

W represents a member selected from the group consisting of:

a) trifluoromethyl group: $—CF_3$;

b) a halogen atom: —Br, —Cl, —F, or 13 I;

c) C1–C4 alkoxy radical: —OC1–4 alkyl, wherein the alkyl is optionally mono-substituted by $R^q$, where $R^q$ is as defined above;

d) a hydroxy group: —OH;

e) a carbonyloxy radical: $—OC(O)R^s$, where $R^s$ is C1–4 alkyl or phenyl, each of which is optionally mono-substituted by $R^q$ as defined above;

f) a carbamoyloxy radical; $—OC(O)N(R^y)R^z$, where $R^y$ and $R^z$ are independently H, C1–4 alkyl, (optionally mono-substituted by $R^q$ as defined above), or are taken together to represent a 3to 5-membered alkylidene radical which forms a ting (optionally substituted with $R^q$ as defined above), or a 2- to 4-membered alkylidene radical interrupted by —O—, —S—, —S(O)— or $—S(O)_2—$ which forms a ring, said ring being optionally mono-substituted with $R^q$ as defined above;

g) a sulfur radical: $—S(O)_n—R^s$, where n=O–2, and $R^s$ is defined above;

h) a sulfamoyl group: $—SO_2N(R^y)R^z$, where $R^y$ and $R^z$ are as defined above;

i) azido: N3 j) a formamido group: $—N(R^t)C(O)H$, where $R^t$ is H or C1–4 alkyl, said alkyl group being optionally mono-substituted with $R^q$ as defined above;

k) an alkylcarbonylamino radical: $—N(R^t)C(O)C1–4$ alkyl, wherein $R^t$ is as defined above;

an alkoxycarbonylamino radical:

$—N(R^t)C(O)OC1–4$ alkyl, where $R^t$ is as defined above;

m) a ureido group: $—N(R^t)C(O)N(R^y)R^z$ where $R^t$, $R^y$ and $R^z$ are defined above;

n) a sulfonamido group: $—N(R^t)SO_2R^s$, where $R^s$ and $R^t$ are as defined above;

o) a cyano group: —CN;

p) a formyl or acetalized formyl radical: —C(O)H or $—CH(OCH_3)_2$;

q) an alkylcarbonyl radical wherein the carbonyl is acetalized: $—C(OCH_3)_2$ C1–C4 alkyl, where the alkyl is optionally mono-substituted by $R^q$ as defined above;

r) a carbonyl radical: $—C(O)R^s$, where $R^s$ is as defined above;

s) a hydroximinomethyl radical in which the oxygen or carbon atom is optionally substituted by a C1–C4 alkyl group: $—(C=NOR^z)R^y$ where $R^y$ and $R^z$ are as defined above, except they may not be joined together to form a ring;

t) an alkoxycarbonyl radical: —C(O)OC1–4 alkyl, where the alkyl is optionally mono-substituted by $R^q$ as defined above;

u) a carbamoyl radical: $—C(O)N(R^y)R^z$, where $R^y$ and $R^z$ are as defined above;

v) an N-hydroxycarbamoyl or N(C1–C4 alkoxy)carbamoyl radical in which the nitrogen atom may be additionally substituted by a C1–C4 alkyl group: $—C(O)N(OR^y)R^z$, where $R^y$ and $R^z$ are as defined above, except they may not be joined together to form a ring;

w) a thiocarbamoyl group: $—C(S)N(R^y)R^z$ where $R^y$ and $R^z$ are as defined above;

x) carboxyl: $—COOM^a$ where $M^a$ is as defined above;

y) thiocyanate: —SCN;

z) trifluoromethylthio: $—SCF_3$;

aa) tetrazolyl, where the point of attachment is the carbon atom of the tetrazole ring and one of the nitrogen atoms is mono-substituted by hydrogen, an alkali metal or a C1–C4 alkyl optionally substituted by $R^q$ as defined above;

ab) an anionic function selected from the group consisting of: phosphono $[P{=}O(OM^a)_2]$; alkylphosphono { $P{=}O(OM^a)—[O(C1–C4$ alkyl)]}; alkylphosphinyl $[P{=}O(OM^a)$-(C1–C4 alkyl)]; phosphoramido $[P{=}O(OM^a)N(R^y)R^z$ and $P{=}O(OM^a)NHR^x]$; sulfino $(SO_2M^a)$; sulfo $(SO_3M^a)$; acylsulfonamides selected from the structures $SO_2NM^aCON(R^y)R^z$; and $SO_2NM^aCN$, where $R^x$ is phenyl or heteroaryl, where heteroaryl is a monocyclic, aromatic hydrocarbon group having 5 or 6 ring atoms, in which a carbon atom is the point of attachment, one of the carbon atoms has been replaced by a nitrogen atom, one additional carbon atom is optionally replaced by a heteroatom selected from O or S, and from 1 to 2 additional carbon atoms are optionally replaced by nitrogen heteroatoms, and where the phenyl and heteroaryl are optionally mono-substituted by $R^q$, said $R^q$, $M^a$, $R^y$ and $R^z$ being as defined above;

ac) a C5–C7 cycloalkyl group in which one of the carbon atoms in the ring is replaced by a heteroatom selected from O, S, NH, or N(C1–C4 alkyl) and in which one additional carbon may be replaced by the NH or N(C1–C4 alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) a C2–C4 alkenyl radical, optionally mono-substituted by one of the substituents a) to ac) above and phenyl which is optionally substituted by $R^q$ as defined above;

ae) a C2–C4 alkynyl radical, optionally mono-substituted by one of the substituents a) to ac) above;

af) a C1–C4 alkyl radical;

ag) a C1–C4 alkyl group mono-substituted by one of the substituents a)– ac) above;

ah) a C1–C6 alkyl group substituted with up to 3 groups selected from oxime (=N-$OR^{14}$), cycloalkyl, aryl, heterocycloalkyl, heteroaryl and C1–3 alkoxy groups;

ai) a 2-oxazolidinonyl moiety in which the point of attachment is the nitrogen atom of the oxazolidinone ting, the ring oxygen atom is optionally replaced by a heteroatom selected from S and $NR^t$ (where $R^t$ is as defined above) and one of the saturated carbon atoms of the oxazolidinone ring is optionally mono-substituted by one of the substituents a) to ag) above, and M represents hydrogen, a negative charge, a biolabile ester forming group, a carboxyl protecting group or a pharmaceutically acceptable cation.

2. The compound of claim 1, wherein one $R^1$ group is selected from:

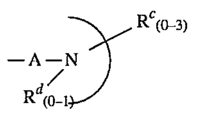

(a)

and

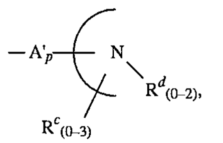

(b)

in which A and A' represent —$CH_2$—, —$CH_2CH_2$— or —$CH_2CH_2CH_2$—;

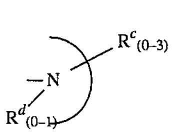

represents

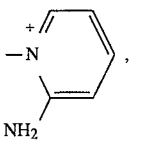

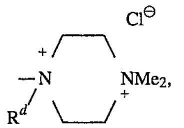

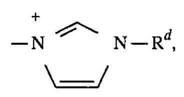

or

-continued

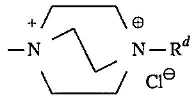

and

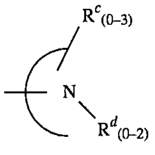

represents

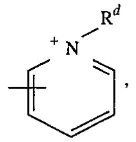

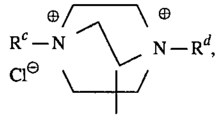

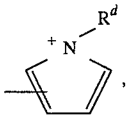

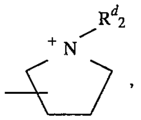

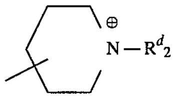

or

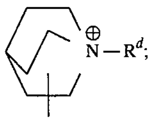

and the point of attachment to —A'— is other than a nitrogen heteroatom.

3. A compound of claim 1, wherein X represents —$CH_2$— and the group —A'— represents —$(CH_2)_m$—X—$(CH_2)_n$— having the value: —$CH_2$—O—; —$CH_2CH_2$—; —$CH_2NH$—; —$CH_2SO_2$—; —$CH_2C(O)$— or —$CH_2OC(O)$—.

4. A compound of claim 2, wherein one $R^1$ variable represents group (a) or (b), one represents hydrogen, and one represents a member selected from the group consisting of:

H; —$CF_3$; —Br; —I; —Cl; —F; —$OC_{1-4}$alkyl; —$OC_{1-4}$ alkyl substituted with 1–3 $R^q$ groups, which are independently selected from —OH, —$OCH_3$, —CN, —F, —$CF_3$, and —$COOM^a$, where $M^a$ is H, alkali metal or methyl; —OH; —$S(O)_xR^s$ with x=0 or 2 and $R^s$= $C_{1-4}$ alkyl; —$C_{2-4}$ alkenyl; —$C_{2-4}$ alkynyl; —$C_{1-4}$ alkyl substituted with —$CF_3$, —Br, —I, —F, Cl or —$OCH_3$; and —C(O)—$C_{1-4}$alkyl.

5. A compound of claim 2, wherein one R1 variable represents group (c) or (d), one represents hydrogen and one represents a member selected from the group consisting of:

H; —$CF_3$; —Br; —I; —Cl; —F; —$OC_{1-4}$ alkyl; —$OC_{1-4}$ alkyl substituted with 1–3 $R^q$ groups, which are independently selected from —OH, —$OCH_3$, —N, —F, —$CF_3$, and —$COOM^a$, where $M^a$ is H, alkali metal or methyl; —OH; —$S(O)_xR^s$ with x=0 or 2 and $R^s$=$C_{1-4}$ alkyl; —$C_{2-4}$ alkenyl; —$C_{2-4}$ alkynyl; —$C_{1-4}$ alkyl substituted with —$CF_3$, —Br, —I, —F, Cl or —$OCH_3$; and —C(O)—$C_{1-4}$ alkyl.

6. A compound of claim 1, wherein one $R^1$ variable represents a substituent selected from:

—$A'_p$—$N(CH_3)_2$, —$A'_p$—$N(CH_2CH_3)_2$, —$A'_p$—$N(CH_3)CH_2R^q$, —$A_p$—$^+N(CH_2CH_3)CH_2CH_2R^q$,

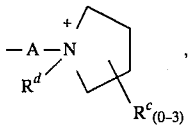
,

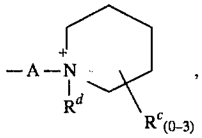
,

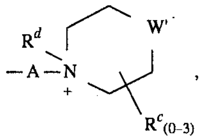
,

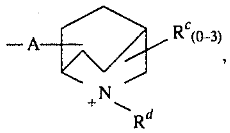
,

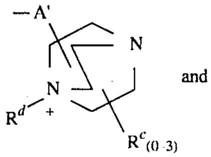
and

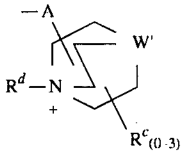

in which W' is O, S, NR', N(O)$R^e$, SO or $SO_2$ , and where $A'_p$— and $R^c$ are shown to have an indefinite position, they may bc attached to any carbon atom of the .ring.

7. A compound of claim 1, wherein one $R^1$ group represents a member selected from the group consisting of:

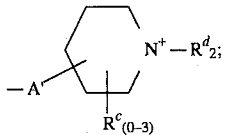
;

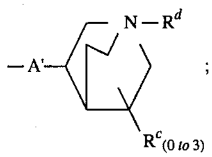
;

-continued

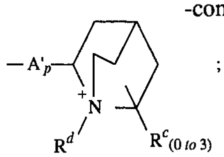
;

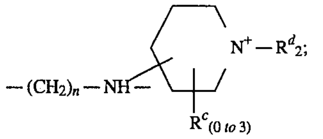
and

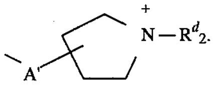

and where $R^c$ and/or A' is shown to have an indefinite position, they may be attached to any carbon atom of the ting.

8. A compound of claim 7, wherein the $R^c$ substituents attached to ring carbon atoms are selected from the group consisting of:

— $NH_2$, —$SCH_3$, —$SOCH_3$, —$CH_2OH$, —$(CH_2)_2OH$, —$OCH_3$, —$COOM^b$, —$CH_2COOM^b$, —$CH_2CH_2COOM^b$, —$CH_2SOCH_3$, —$CH_2SCH_3$, —$SO_3M^b$, —$CH_2SO_3M^b$, —$CH_2CH_2SO_3M^b$, —Br, —Cl, —F, —I, —$CH_3$, —$CH_2CH_3$, —$CH_2CONH_2$ and —$CH_2CON(C_1$-$C_4$ alkyl$)_2$ , and the $R^d$ substituents attached to ring nitrogen atoms are selected from the group consisting of: —$CH_2OH$, —$(CH_2)_2OH$, —$CH_2COOM^b$, —$CH_2CH_2COOM^b$, —$CH_2SOCH_3$, —$CH_2SCH_3$, —$CH_2SO_3M^b$, —$CH_2CH_2SO_3M^b$, —$CH_3$, —$CH_2CH_3$, —$CH_2CONH_2$ and —$CH_2CON(C_1$-$C_4$ alkyl).

9. A compound of claim 8 wherein the $R^d$ substituents attached to the nitrogen atom are selected from the group consisting of: hydrogen, —$CH_3$, —$CH_2CH_3$, —$CH_2CH_2CH_3$, —$CH_2COOM^b$, $CH_2C(O)NH_2$, —$CH_2SO_2NH_2$; —$CH_2SO_3M^b$, —$NH_2$ and —O—.

10. A compound of claim 2, wherein —A— is selected from the group consisting of:

—$CH_2$—, —$CH_2CH_2$—, —$CH_2CH_2CH_2$—, —$CH_2CH_2CH_2$ $CH_2$—, —$OCH_2CH_2$—, —$SOCH_2$—, —$SO_2CH_2$—, —$SCH_2CH_2$—, —$SOCH_2$ $CH_2$—, —$SO_2CH_2CH_2$—, 13 $NHCH_2CH_2$—, —$N(CH_3)CH_2CH_2$—, —$CH_2N(CH_3)CH_2CH_2$—, —$SO_2NHCH_2CH_2$—, —$COCH_2$—, —CH=$CHCH_2$— and —$CH_2$—O—$CH_2CH_2$—.

11. A compound of claim 1, wherein —A'—, is selected from the group consisting of:

—0—, —S—, —NH—, —$SO_2$—, —$SO_2NH$—, —CONH—, —CH=CH—, —$CH_2S$—, —$CH_2NH$—, $CONHCH_2$—, —$SO_2NHCH_2$—, —$CH_2$—, —$CH_2CH_2$—, —$CH_2CH_2CH_2$—, —$CH_2CH_2CH_2CH_2$—, —$OCH_2CH_2$—, —$SOCH_2$—, —$SO_2CH_2$—, —$SCH_2CH_2$—, —$SOCH_2CH_2$—, —$SO_2CH_2CH_2$—, —$NHCH_2CH_2$—, —$N(CH_3)CH_2CH_2$—, —$CH_2N(CH_3)CH_2CH_2$—, —$SO_2NHCH_2CH_2$—, —$COCH_2$—, —CH=$CHCH_2$— and —$CH_2$—O—$CH_2CH_2$—.

12. A compound of claim 1, wherein one of the $R^1$ groups represents one of (a) through (d) and the other $R^1$ groups are independently selected from:

| | |
|---|---|
| $-OCH_3$ | |
| $-OCH_2CH_2OH$ | $-OCH_2CO_2Me$ |
| —F | $-CF_3$ |
| —Br | —Cl |
| —OH | —I |
| $-OCONH_2$ | $-OCOCH_3$ |
| $-SOCH_3$ | $-SCH_3$ |
| $-SCH_2CH_2OH$ | $-SO_2CH_3$ |
| $-SO_2NH_2$ | $-SOCH_2CH_2OH$ |
| —NHCHO | $-SO_2N(CH_3)_2$ |
| $-NHCO_2CH_3$ | $-NHCOCH_3$ |
| —CN | $-NHSO_2CH_3$ |
| $-COCH_3$ | —CHO |
| —CH=NOH | $-COCH_2OH$ |
| $-CH{=}NOCH_2CO_2Me$ | $-CH{=}NOCH_3$ |
| $-SO_2CH_2CH_2OH$ | $-CH{=}NOCMe_2CO_2Me$ |
| $-CH{=}NOCMe_2CO_2Me$ | $-CO_2CH_2CH_2OH$ |
| $-CONH_2$ | $-CONHCH_3$ |
| $-CON(CH_3)_2$ | $-CONHCH_2CN$ |
| $-CONHCH_2CONH_2$ | $-CONHCH_2CO_2Me$ |
| —CONHOH | $-CONHCH_3$ |
| -tetrazolyl | $-CO_2Me$ |
| $-SCF_3$ | $-PO_3HMe$ |
| $-CONHSO_2Ph$ | $-CONHSO_2NH_2$ |
| $-SO_3Me$ | $-SO_2NHCN$ |
| $-SO_2NHCONH_2$ | —CH=CHCN |
| $-CH{=}CHCONH_2$ | $-CH{=}CHCO_2Me$ |
| $-C{\equiv}C-CONH_2$ | $-C{\equiv}C-CN$ |
| $-CH_2OH$ | $-CH_2N_3$ |
| $-CH_2CO_2Me$ and | $-CH_2I$. |

13. A compound according to claim 1, wherein M is $Na^+$, $K^+$ or a negative charge.

14. A pharmaceutical composition comprising a compound of claim 1 in combination with a pharmaceutically acceptable carrier.

15. A method of treating a bacterial infection in a mammal in need of such treatment, comprising administering to said mammal a compound of claim 1 in an amount effective to treat said bacterial infection.

16. A pharmaceutical composition comprising a compound of claim 1 and a DHP inhibitor in combination with a pharmaceutically acceptable carrier.

17. A pharmaceutical composition according to claim 16 wherein the DHP inhibitor is 7-(L-2-amino-2-carboxyethylthio)-2-(2, 2-dimethylcyclopropanecarboxamide)- 2-heptenoic acid.

18. A method of treating a bacterial infection in a mammal in need of such treatment, comprising administering to said mammal an antibacterially effective amount of a compound of claim 1 and an inhibitorily effective amount of a DHP inhibitor.

19. A method according to claim 18, wherein the DHP inhibitor is 7-(L-2-amino-2-carboxyethyl- thio)-2-(2, 2-dimethylcyclopropanecarboxamide)- 2-heptenoic acid.

* * * * *